(12) United States Patent
Thurbide

(10) Patent No.: US 8,913,239 B2
(45) Date of Patent: Dec. 16, 2014

(54) APPARATUS AND METHOD FOR QUENCHING-RESISTANT MULTIPLE FLAME PHOTOMETRIC DETECTOR

(75) Inventor: Kevin Thurbide, Calgary (CA)

(73) Assignee: UTI Limited Partnership, Calgary (CA)

( * ) Notice: Subject to any disclaimer, the term of this patent is extended or adjusted under 35 U.S.C. 154(b) by 298 days.

(21) Appl. No.: 13/041,191

(22) Filed: Mar. 4, 2011

(65) Prior Publication Data

US 2011/0239737 A1    Oct. 6, 2011

Related U.S. Application Data

(60) Provisional application No. 61/310,982, filed on Mar. 5, 2010.

(51) Int. Cl.
*G01J 3/30* (2006.01)
*G01N 30/68* (2006.01)

(52) U.S. Cl.
CPC .......... *G01N 30/68* (2013.01); *G01N 2030/685* (2013.01)
USPC .......................................... 356/315; 356/213

(58) Field of Classification Search
CPC . G01N 2030/685; G01N 21/72; G01N 30/68; G01N 2030/025; G01R 33/4838; G01R 33/5602; G01R 33/5607
USPC .......................................... 436/160, 164, 172
See application file for complete search history.

(56) References Cited

U.S. PATENT DOCUMENTS

| 4,097,239 | A | 6/1978 | Patterson | 436/106 |
| 4,234,257 | A | 11/1980 | Carter et al. | 356/417 |
| 4,311,664 | A | 1/1982 | Zaremba et al. | 422/54 |
| 2005/0287033 | A1 | 12/2005 | Thurbide | 422/51 |

OTHER PUBLICATIONS

Aue and Sun, "Spectrum, multi-element selectivity and elemental response of a linear sulfur emitter in flame photometry," *J. Chromatogr A.*, 633:151-162, 1993.
Aue and Sun, "Quenching in the flame photometric detector," *J. Chromatogr. A.*, 641:291-299, 1993.
Baruah and Khare, "Pyrolysis of high sulfur indian coals," *Energy and Fuels*, 21:3346-3352, 2007.
Brody and Chaney, "Flame photometric detector : the application of a specific detector for phosphorous and for sulfur compounds—sensitive to subnanogram quantities," *J. Gas Chromatogr.*, 4:42-46, 1966.
Burnett et al., "Relative FPD Responses for a Systematic Group of Sulfur-Containing Compounds ," *J. Chromatogr.*, 16:68-73, 1978.
Chen et al., "Degradation behaviour of methamidophos and chlorpyrifos in apple juice treated with pulsed electric fields," *Food Chemistry*, 112:956-961, 2009.
Cheskis et al., "Pulsed-flame photometer: a novel gas chromatography detector," *Anal. Chem.*, 65:539-555, 1993.
Clay et al., "Determination of total sulfur in gasoline by gas chromatography with a flame photometric detector," *Anal Chem.*, 49:126-128, 1977.
Dressler, In: *Selective Gas Chromatographic Detectors*, Elsevier: Amsterdam, 153-157, 1986.

(Continued)

*Primary Examiner* — Yelena G Gakh
(74) *Attorney, Agent, or Firm* — Parker Highlander PLLC

(57) ABSTRACT

Provided herein are apparatuses and methods regarding photometric analyte detection using multiple flames, including a multiple flame photometric detector (mFPD). Such a detector may be used, for example, to detect sulfur and phosphorous in effluent streams containing hydrocarbons.

62 Claims, 8 Drawing Sheets

(56) References Cited

OTHER PUBLICATIONS

Farwell and Baringa, "Sulfur-selective detection with the fpd: current enigmas, practical usage, and future directions," *J. Chromatogr Sci.*, 24:483-494, 1986.

Ferguson and Luke, "Critical appraisal of the flame photometric detector in petroleum analysis," *Chromatographia*, 12:197-203, 1979.

Fuentes et al., "Suitability of microwave-assisted extraction coupled with solid-phase extraction for organophosphorus pesticide determination in olive oil," *J. Chromatogr. A.*, 1207:38-45, 2008.

Hayward and Thurbide, "Characteristics of sulfur response in a micro-flame photometric detector," *J. Chromatogr. A.*, 1105:66-70, 2006.

Hayward and Thurbide, "Novel on-column and inverted operating modes of a microcounter-current flame ionization detector," *J. Chromatogr. A.*, 1200:2-7, 2008.

Hayward and Thurbide, "Carbon response characteristics of a micro-flame ionization detector," *Talanta*, 73:583-588, 2007.

Hayward and Thurbide, "Quenching-resistant multiple micro-flame photometric detector for gas chromatography," *Anal. Chem.*, 81:8858-8867, 2009.

Kalontrov et al., "Mechanism of sulfur emission quenching in flame photometric detectors," *J. Chromatagr. A.*, 696:245-256, 1995.

Kendler et al., "Ultrafast Gas Chromatographic Separation of Organophosphor and Organosulfur Compounds Utilizing a Microcountercurrent Flame Photometric Detector," *Anal. Chem.*, 78:6765-6773, 2006.

Kendler et al., "A new method and apparatus for on-site detection of trace levels of chemical warfare agents," *Anal. Chim. Acta*, 548:58-65, 2005.

Nishikawa et al., "Isocratic separation of adenosine 5'-triphosphate and its metabolites by reversed-phase high performance liquid chromatography: end-capped versus uncapped packings," *Anal Sci.*, 7:241-244, 1991.

Li et al., "Use of graphitic carbon black and primary secondary amine for determination of 17 organophosphorus pesticide residues in spinach," *J. Sep. Sci.*, 31:3588-3594, 2008.

Logan et al., "A method for the analysis of tabun in multisol using gas chromatographic flame photometric detection," *Toxicol Mech Methods.*, 16:359-363, 2006.

McGuffin and Novotny, "Flame emission detection in microcolumn liquid chromatography," *Anal. Chem.*, 53:946-951, 1981.

Olesik et al., "Characterization and optimization of flame photometric detection in supercritical fluid chromatography," *Anal. Chem.*, 61:58-65, 1989.

Patterson et al., "Dual-flame photometric detector for sulfur and phosphorus compounds in gas chromatograph effluents," *Anal. Chem.*, 50:339-344, 1978.

Patterson et al., "Comparison of quenching effects in single- and dual-flame photometric detectors," *Anal. Chem.*, 50:345-348, 1978.

Pearson and Hines, "Determination of hydrogen sulfide, carbonyl sulfide, carbon disulfide, and sulfur dioxide in gases and hydrocarbon streams by gas chromatography/flame photometric detection," *Anal. Chem.*, 49:123-126, 1977.

Poole and Schutte, In *Contemporary Practice of Chromatography*, Elsevier, Amsterdam, 187, 1984.

Rupprecht and Phillips, "The utilisation of fuel rich flames as sulphur detectors," *Anal. Chim. Acta*, 47:439-449, 1969.

Seto et al., "Development of an on-site detection method for chemical and biological warfare agents," *Toxin Reviews*, 26:299-312, 2007.

Sevcik and Thao, "The selectivity of the flame photometric detector," *Chromatographia*, 8:559-562, 1975.

Sugiyama et al., "Characteristics of $S_2$ emission intensity with a flame photometric detector," *J. Chromatogr. A.*, 77:309-316, 1973.

Sugiyama et al., "Interferences of $S_2$ molecular emission in a flame photometric detector," *J. Chromatogr. A.*, 80:61-67, 1973.

Sun et al., "Flame photometric detection of some transition metals. I. Calibrations and spectra," *Can. J. Chem.*, 70:1129-1142, 1992.

Thurbide and Anderson, "Flame photometric detection inside of a capillary gas chromatography column," *Analyst*, 128: 616-622, 2003.

Thurbide and Aue, "Quenching-free reactive-flow photometry," *J. Chromatogr. A.*, 694:433-440, 1995.

Thurbide and Hayward, "Improved micro-flame detection method for gas chromatography," *Anal. Chim. Acta.*, 519:121-128, 2004.

Thurbide et al., "Novel flame photometric detector for gas chromatography based on counter-current gas flows," *J. Chromatogr. A.*, 1029:193-203, 2004.

Tolosa et al., "Organotin speciation in aquatic matrices by CGC/FPD, ECD and MS, and LC/MS," *Fresenius J. Anal. Chem.*, 339:646-653, 1991.

Tuan et al., "Determination of sulfur components in natural gas: A review," *J. High. Resol. Chromatogr.*, 17:373-389, 1994.

Wang et al., "Desulfurization of jet fuel jp-5 light fraction by MCM-41 and SBA-15 supported cuprous oxide for fuel cell applications," *Ind. Eng. Chem. Res.*, 48:142-147, 2009.

Zhao et al., "Photochemical oxidation—ionic liquid extraction coupling technique in deep desulphurization of light oil," *Energy Fuels*, 22:1100-1103, 2008.

FIGS. 1A-B

APPARATUS AND METHOD FOR QUENCHING-RESISTANT MULTIPLE FLAME PHOTOMETRIC DETECTOR

The present application claims the benefit of priority to U.S. Provisional Application No. 61/310,982 filed Mar. 5, 2010, the entire content of which is incorporated herein by reference in its entirety.

BACKGROUND OF THE INVENTION

I. Field of the Invention

This invention relates to gas chromatography and more particularly relates to an apparatus and method for gas detection using a quenching-resistant multiple flame photometric detector.

II. Description of the Related Art

For gas chromatography (GC), there exist a variety of detectors that can provide information regarding sample composition. A flame-based device that is very widely used in the selective analysis of sulfur and phosphorus compounds is the relatively robust and inexpensive flame photometric detector (FPD). First developed by Brody and Chaney several decades ago (Brody and Chaney, 1966), the FPD has evolved into a reliable tool that is still prevalently used in many important areas such as the analysis of pesticides (Li et al., 2008; Fuentes et al., 2008; Chen et al., 2008), petroleum (Wang et al., 2009; Zhao et al., 2008; Baruah and Khare, 2007), and chemical warfare agents (Seto et al., 2007; Logan et al., 2006; Kendler et al., 2005).

One of the strengths of the FPD is its ability to selectively detect lower quantities of sulfur and phosphorus analytes relative to other hydrocarbons (Brody and Chaney, 1966; Sevcik and Thao, 1975). However, it also has some disadvantages. For instance, although linear operating regions can be accessed (Aue and Sun, 1993), conventional FPD sulfur response is often pseudo-quadratic due to the predominant chemiluminescence of $S_2$ produced in the hydrogen-rich flame (Farwell and Barinaga, 1986). Further, the yield of this species is dependent upon burner design, gas flows, analyte concentration and molecular structure. Also, its response can vary among individual compounds, leading to a relatively non-uniform response factor over a broad range of sulfur analytes (Sugiyama et al., 1973; Burnett et al., 1978).

A further drawback is that analyte chemiluminescence in the FPD is typically quenched in the presence of even moderate amounts of co-eluting hydrocarbons (Dressler, 1986; McGuffin and Novotny, 1981; Pearson and Hines, 1977; Clay et al., 1977). As such, this can complicate the analysis of complex samples, since the complete separation of analytes from all matrix components is often impractical. Although the mechanism for this response quenching is still not fully established, several possibilities have been suggested (Kalontrov et al., 1995; Aue and Sun, 1993; Sugiyama et al., 1973; Cheskis et al., 1993). Nonetheless, the resulting FPD signal erosion observed can present serious problems for the analyst.

Of the various kindred FPD devices reported over the years, occasionally those based upon unconventional combustion dynamics, such as the pulsed-FPD (Kalontrov et al., 1995; Cheskis et al., 1993) and the reactive flow detector (Thurbide and Aue, 1995), have been demonstrated to reduce the effect of hydrocarbon quenching. Perhaps the most widely investigated device in this regard is the dual-flame FPD (dFPD) (Rupprecht and Phillips, 1969; Patterson et al., 1978; Patterson, 1978; Machino, 1996; Koizumi and Suzuki, 1991; Tolosa et cd., 1991; Poole, 2003; Poole and Schuette, 1984; Ferguson and Luke, 1979; Tuan et al., 1994), which is based upon two flames placed in series. In the dFPD, the lower flame is normally optimized to oxidize hydrocarbons toward carbon dioxide formation, while the upper flame is optimized to produce analyte chemiluminescence for measurement. The result is a reduction in analyte response quenching and a more uniform, reproducible response (Poole, 2003).

When first developed by Rupprecht and Phillips (1969), the consecutive oxygen-rich then hydrogen-rich dFPD flame environments employed produced negligible hydrocarbon quenching toward sulfur chemiluminescence. In their report, they concluded that quenching is greatly reduced when carbon is present as carbon dioxide versus a less oxidized hydrocarbon (Rupprecht and Phillips, 1969). Subsequently, Patterson et al. (1978) expanded upon this by designing a dFPD that easily converts to a single flame FPD as needed (Patterson et al., 1978; Patterson, 1978). This dFPD model demonstrated several advantages including similar optimal flame gas flows for sulfur and phosphorus detection and a more uniform response, as well as the reduced hydrocarbon quenching that was noted earlier (Rupprecht and Phillips, 1969). Thus, the dFPD offers some useful properties and is often regarded as a quenching-free device for practical applications (Kalontrov et al., 1995), particularly those dealing with elevated hydrocarbon levels (Patterson, 1978).

Despite these benefits, however, the dFPD has some significant disadvantages. For example, dFPD burner designs are often somewhat bulky and complex, and in some cases may require a rather elaborate ignition sequence to initially establish the dual flames (Rupprecht and Phillips, 1969; Patterson et al., 1978). In particular, these features can inhibit incorporation of this technology into miniaturized/portable analytical devices. However, of much greater concern, the dFPD is widely reported to produce significantly reduced detector sensitivity relative to a conventional FPD (Rupprecht and Phillips, 1969; Patterson, 1978; Poole, 2003; Poole and Schuette, 1984; Ferguson and Luke, 1979; Tuan et al., 1994). Given the noted advantages of the dFPD, it would be beneficial if these problems could be overcome. There is a need in the industry for a compact simple detector that would easily establish consecutive flames.

Recently, a micro counter-current FPD (µFPD) method was introduced that is based upon relatively small opposing flows of hydrogen and oxygen (Thurbide et al., 2004; Thurbide and Anderson, 2003; Thurbide and Hayward, 2004; Hayward and Thurbide, 2006). As such, this arrangement can produce a very tiny (~30 nL) flame that resides 'upside down' on a stainless steel capillary delivering oxygen in a counter-flowing stream of hydrogen. Once established, the micro flame is capable of producing both chemiluminscent and ionization responses that are respectively very similar to the conventional Flame Photometric and Flame Ionization (FID) Detectors (Thurbide and Hayward, 2004; Hayward and Thurbide, 2007; Hayward and Thurbide, 2008). As a result, this device can potentially provide a relatively simple, robust, and sensitive FPD method in a micro analytical format (Thurbide and Hayward, 2004; Hayward and Thurbide, 2008). Table 1 summarizes its properties relative to an FPD and dFPD.

TABLE 1

Characteristics of Single, Dual, and Micro-Flame Photometric Detectors

| Photometric Detector | Advantages | Disadvantages |
| --- | --- | --- |
| Single Flame (FPD) | Good sensitivity<br>Simple operation | Significant quenching<br>Limited response uniformity<br>Limited reproducibility<br>Limited portability |
| Dual Flame (dFPD) | Reduced quenching<br>Improved response uniformity<br>Improved reproducibility | Reduced sensitivity<br>Increased complexity<br>Limited portability |

TABLE 1-continued

Characteristics of Single, Dual, and Micro-Flame Photometric Detectors

| Photometric Detector | Advantages | Disadvantages |
|---|---|---|
| Micro Flame (μFPD) | Good sensitivity<br>Simple operation<br>Good portability | Significant quenching<br>Limited response uniformity<br>Limited reproducibility |

The referenced shortcomings are not intended to be exhaustive, but rather are among many that tend to impair the effectiveness of previously known techniques in flame photometric detectors; however, those mentioned here are sufficient to demonstrate that the methodologies appearing in the art have not been satisfactory and that a significant need exists for the techniques described and claimed in this disclosure.

SUMMARY OF THE INVENTION

Disclosed herein are multiple flame photometric detectors (mFPDs) and methods of use thereof. In one aspect, there is provided a mFPD, comprising:
(a) a conduit comprising
  (1) three or more oxygen inlets, comprising
    i) a first oxygen inlet;
    ii) a second oxygen inlet;
    ii) a final oxygen inlet;
  (2) a hydrogen inlet;
  (3) a detector port;
  (4) an analyte inlet; and
(b) a light detector configured to detect emissions through the detector port.

In some embodiments, each oxygen inlet is coupled to an oxygen tube. Each oxygen tube may be in fluid connection with an oxygen source. In some embodiments, one or more of the oxygen tubes is a stainless steel tube. In some embodiments, the conduit and one or more of the oxygen tubes are made from the same material, for example, stainless steel or quartz. In some embodiments, the conduit and one or more of the oxygen tubes are comprised from a unitary piece. In other embodiments, the conduit and one or more of the oxygen tubes are separate components.

In some embodiments, one or more tubes may be made of glass. In some embodiments, each oxygen tube has an inner diameter from about 0.05 mm to about 5 mm. In some embodiments, the inner diameter is about 0.25 mm. In other embodiments, at least one flame resides at an oxygen tube during use. A flame may reside at the end of one or more oxygen tubes. In some embodiments, the size of one or more of the flames is between about 3 nL to 1 mL. In some embodiments, the size of one or more of the flames is about 30 nL. In some embodiments, the cross section of one or more of the flames through its center occupies from 50% to 95% of the cross section of the conduit. In some embodiments, the cross section of one or more of the flames through its center occupies from 60% to 85% of the cross section of the conduit. In some embodiments, the cross section of one or more of the flames through its center occupies about 75% of the cross section of the conduit.

The conduit has two ends: a proximal end and a distal end. During operation, an effluent gas will typically flow from the proximal end to the distal end. In some embodiments, the final oxygen inlet is closer to the distal end of the conduit than to the first and second oxygen inlets. In some embodiments, the first oxygen inlet is to the proximal end of the conduit than the second oxygen inlet. In some embodiments, a flame closest to the distal end of the conduit functions as an analytical flame. The analytical flame may reside at the end of an oxygen tube coupled to the final oxygen inlet. In some embodiments, the first and second flames from the proximal end of the conduit function as worker flames. The first worker flame may be closer to the proximal end of the conduit and the second worker flame may be between the first worker flame and the analytical flame. The first worker flame may reside at the end of the oxygen tube coupled to the first oxygen inlet. The second worker flame may reside at the end of the oxygen tube coupled to the second oxygen inlet. In some embodiments, there may be more than two worker flames and each worker flame is closer to the proximal end of the conduit than the analytical flame. The effluent gas may come into contact with the worker flames before coming into contact with the analytical flame.

In some embodiments, there are one or more bends in the conduit between the final oxygen inlet and the next closest oxygen inlet along the length of the conduit. In some embodiments, each bend has an angle from 30 to 360 degrees. In some embodiments, there are three 90 degree bends in the conduit between the final oxygen inlet and the next closest oxygen inlet along the length of the conduit. In some embodiments, during use, a worker flame resides at the tube coupled to the first oxygen inlet and a worker flame resides at the tube coupled to the second oxygen inlet.

In some embodiments, the conduit is constructed from one or more materials. The conduit may comprise quartz. In some embodiments, the conduit is quartz, glass, stainless steel, ceramic or silicon. In some embodiments, the conduit has a cylindrical shape. In some embodiments, the shape of some or all of the conduit is a circular cylinder, an elliptic cylinder, a parabolic cylinder, or a hyperbolic cylinder. In some embodiments, the cross section of some or all of the conduit has a semi-circular shape. In some embodiments, the cross section of some or all of the conduit has a shape as would result from an etching procedure. In some embodiments, the conduit has an inner diameter from about 0.1 mm to about 10 mm. The inner diameter may be about 1 mm. In some embodiments, the conduit has a length from about 5 mm to about 1,000 mm. The length may be about 130 mm.

In some embodiments, the final oxygen inlet is separated from the second oxygen inlet by a first distance of about 2 mm to about 50 mm. The first distance between the final oxygen inlet and the second oxygen inlet may be about 20 mm. In some embodiments, the first oxygen inlet and the second oxygen inlet are separated by a second distance of about 1 mm to about 20 mm. The second distance may be about 5 mm. In some embodiments, the conduit has four oxygen inlets, for example, a first, a second, a third and a final oxygen inlet. In some embodiments, the conduit has five oxygen inlets, for example, a first, a second, a third, a fourth and a final oxygen inlet. In some embodiments, the conduit has six oxygen inlets, for example, a first, a second, a third, a fourth, a fifth and a final oxygen inlet. In some embodiments, the hydrogen inlet is positioned closer to the proximal end of the conduit than the oxygen inlets. In some embodiments, the hydrogen inlet is in fluid connection with a hydrogen source. In some embodiments, the analyte inlet is positioned closer to the proximal end of the conduit than the oxygen inlets.

In some embodiments, the mFPD is capable of detecting sulfur at a concentration of less than $1 \times 10^{-10}$ g S/s during use. In some embodiments, the mFPD is capable of detecting phosphorus at a concentration of less than $1 \times 10^{-11}$ g P/s during use. In some embodiments, the mFPD is capable of maintaining greater than 50% of the original analyte chemiluminescence even in the presence of up to 100 mL/min of hydrocarbon gas flow into the detector during use. In some embodiments, the apparatus further comprises an igniter coupled to the conduit.

In another aspect, there is provided a method for photometric detection comprising:

(1) delivering an effluent comprising analyte into a conduit comprising:
  (a) three or more oxygen inlets, comprising
    i) a first oxygen inlet;
    ii) a second oxygen inlet;
    ii) a final oxygen inlet;
  where the final oxygen inlet is closest to the distal end of the conduit, the first oxygen inlet is closest to the proximal end of the conduit and the second oxygen inlet is between the first oxygen inlet and the final oxygen inlet;
  where the oxygen inlets are coupled to oxygen tubes in fluid connection with an oxygen source;
  where an analytical flame resides at the tube coupled to the final oxygen inlet and worker flames reside at the tubes coupled to the first oxygen inlet and the second oxygen inlet;
  (b) a hydrogen inlet in fluid connection with a hydrogen source;
  (c) a detector port; and
  (d) an analyte inlet through which an effluent is delivered;
(2) contacting the effluent with the worker flames before contacting the effluent with the analytical flame; and
(3) detecting emissions from the analytical flame through the detector port using a light detector.

In some embodiments, each tube has an inner diameter from about 0.05 mm to about 5 mm. The inner diameter may be about 0.25 mm. In some embodiments, the size of one or more of the flames is between about 3 nL to 1 mL. In some embodiments, the conduit is constructed from one or more materials. For example, the conduit may comprise quartz. In some embodiments, the conduit has an inner diameter from about 0.1 mm to about 10 mm. In some embodiments, the inner diameter is about 1 mm. In some embodiments, the conduit has a length from about 5 mm to about 1,000 mm. In some embodiments, the length is about 130 mm. In some embodiments, the tubes coupled to the first and second oxygen inlets are positioned along the length of the conduit. In some embodiments, the final oxygen inlet is separated from the second oxygen inlet by a first distance of about 2 mm to about 50 mm. In some embodiments, the first distance is about 20 mm. In some embodiments, the first and second oxygen inlets are separated by a second distance of about 1 mm to about 20 mm. In some embodiments, the second distance is about 5 mm. In some embodiments, the analytical flame is separated from the second worker flame by a distance of about 2 mm to about 50 mm. In some embodiments, the distance between the analytical flame and the second worker flame is about 20 mm. In some embodiments, the distance between the first and second worker flames is about 1 mm to about 20 mm. In some embodiments, the distance between the first and second worker flames about 5 mm.

In some embodiments, the conduit has four oxygen inlets, for example, a first, a second, a third and a final oxygen inlet. In some embodiments, the conduit has five oxygen inlets, for example, a first, a second, a third, a fourth and a final oxygen inlet. In some embodiments, the conduit has six oxygen inlets, for example, a first, a second, a third, a fourth, a fifth and a final oxygen inlet. In some embodiments, the hydrogen inlet is positioned closer to the proximal end of the conduit than the oxygen inlets.

In some embodiments, the method is capable of detecting sulfur at a concentration of less than $1 \times 10^{-10}$ g S/s during use. In some embodiments, the method is capable of detecting phosphorus at a concentration of less than $1 \times 10^{-11}$ g P/s during use. In some embodiments, the method is capable of maintaining about 50% of its original analyte chemiluminescence even in the presence of up to 100 mL/min of hydrocarbon gas flow into the detector during use.

In some embodiments, a method is provided detecting analyte using a multiple flame photometric detector (mFPD) according to any of the embodiments disclosed herein.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Definitions

Figure 1:
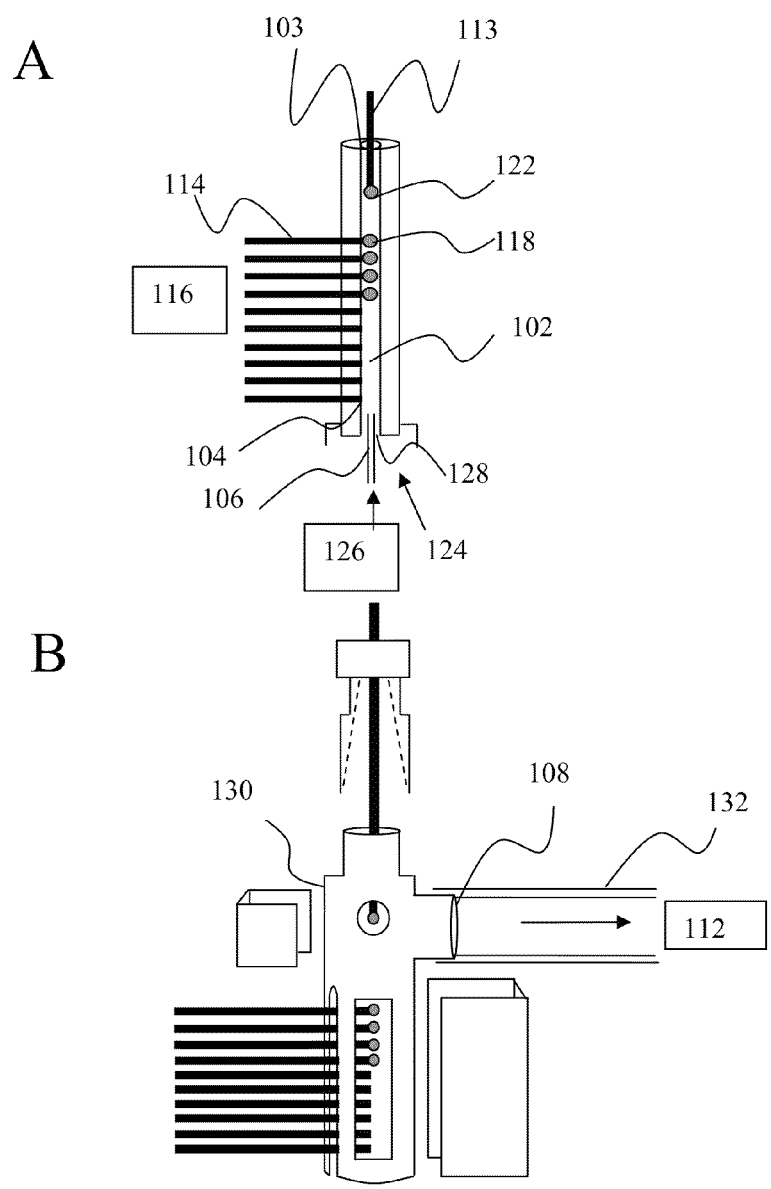
FIG. 1A is a schematic illustration of several components of an mFPD, including a conduit in which the mFPD flames would be enclosed during operation. This figure is discussed in greater detail below.
FIG. 1B is a schematic illustration of several components of an mFPD, including a detector housing. This figure is discussed in greater detail below.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

Quenching-Resistant Multiple Flame Photometric Detectors

All the apparatuses and methods disclosed and/or claimed herein can be made and executed without undue experimentation in light of the present disclosure. While the apparatuses and methods of this invention have been described in terms of certain embodiments, it will be apparent to those of skill in the art that variations may be applied to the methods and in the steps or in the sequence of steps of the methods described herein without departing from the concept, spirit and scope of the invention. In addition, modifications may be made to the disclosed apparatuses, for example, components may be eliminated or substituted for the components described herein where the same or similar results would be achieved. All such similar substitutes and modifications apparent to those skilled in the art are deemed to be within the spirit, scope, and concept of the invention as disclosed herein or defined by the appended claims.

Various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

FIGS. 1A and 1B illustrate embodiments of an apparatus for photometric detection 100. The photometric detector 100 has a conduit 102, which further comprises, three or more oxygen inlets 103 and 104 (pointing to just one of these in the figure), a detector port 108, and an analyte inlet 128. In this illustration, the top of the conduit is the distal end and the bottom of the conduit is the proximal end.

FIG. 1A shows an embodiment of a component of photometric detector 100. In this embodiment, the final oxygen inlet 103 is at the top of the conduit. In this embodiment, final oxygen inlet 103 also serves as the effluent outlet during operation of the apparatus. In other embodiments, the final oxygen inlet and the effluent outlets are separate ports. FIG. 1A also shows one embodiment in which each of oxygen inlets 103 and 104 may be coupled to respective oxygen tubes 113 and 114 (pointing to just one of these in the figure). In some embodiments, one or more of the oxygen tubes 113 and 114 may independently have the shape of a cylinder, a cuboid, or a prism. In some embodiments, the cuboid is a rectangular box. In some embodiments, the cylinder is a circular cylinder, an elliptic cylinder, a parabolic cylinder, or a hyperbolic cylinder. In some embodiments, the cross section of one or more of the oxygen tubes 113 and 114 has a semi-circular shape. In some embodiments, the cross section of one or more of the oxygen tubes 113 and 114 has a shape as would result from an etching procedure. Additionally, the size and/or shape of one or more of the oxygen tubes 113 and 114 may vary along its length. The tubes may be made of stainless steel, glass, quartz, ceramic, silicon or other materials. Each oxygen tube 113 and 114 has an inner diameter that ranges from about 0.05 mm to about 5 mm. In one example, the oxygen tubes have an inner diameter of about 0.25 mm. In some embodiments, each oxygen tube is in fluid connection with an oxygen source 116. The oxygen source 116 may be used to support the combustion of worker flames 118 and/or analytical flame 122. The analytical flame 122 is closer to the distal end of the conduit 102 than the worker flames 118. The size of the worker flames 118 and the analytical flame 122 range from about 3 nL to 1 mL. In some embodiments, the size of the flames can be adjusted by adjusting the flow of the oxygen. In some embodiments, the cross section of a worker flame through its center occupies from 50 to 95% of the cross section of conduit 102, in some it occupies 60% to 85%, and in some it occupies about 75%.

Still referring to FIG. 1A, the analyte inlet 128 is located at the proximal end of the conduit. Effluent gas 124 enters the conduit through the analyte inlet and hydrogen inlet 128. In this embodiment, the hydrogen tube 106 enters through the conduit and/or is coupled to the analyte and hydrogen inlet. In other embodiments, the analyte inlet and the hydrogen inlet may be different inlets or ports. The hydrogen tube is configured to receive hydrogen gas from hydrogen source 126 during operation. Also during operation, effluent gas 124 flows from the proximal end of the conduit to the distal end of the conduit. As the effluent gas 124 travels through the conduit 102 during operation, it first comes into contact with worker flames 118 and then with analytical flame 122. It should be noted, however, that not all oxygen tubes 114 may have worker flames 118 present during operation. In some embodiments, one or more of the oxygen tubes 114 may be turned off or may not be connected to an oxygen source.

Still referring to FIG. 1A, the conduit 102 may be constructed out of one or more of a variety materials, including quartz, glass, stainless steel, ceramic and silicon. In some embodiments, conduit 102 may be cylindrical in shape. In other embodiments, it may have the shape of a cuboid or a prism. In some embodiments, the cuboid is a rectangular box. In some embodiments, the cylinder is a circular cylinder, an elliptic cylinder, a parabolic cylinder, or a hyperbolic cylinders. In some embodiments, the cross section of some or all of the conduit 102 has a semi-circular shape. In some embodiments, the cross section of some or all of conduit 102 has a shape as would result from an etching procedure. Additionally, the size and/or shape of the conduit may vary along its length. For example, the conduit may be one size and/or shape in portions where the worker flames 118 reside and another size and/or shape where the detector port 108 resides. In some embodiments, conduit 102 has an inner diameter, or an average inner diameter, that ranges from about 0.1 mm to about 10 mm and a length from about 5 mm to about 1,000 mm. For example, in one embodiment, conduit 102 has an inner diameter or an average inner diameter of about 1 mm and a length of about 130 mm.

In some embodiments, the final oxygen inlet 103 and the next closest oxygen inlet of oxygen inlets 104 is separated by a first distance of about 2 mm to about 50 mm. In some embodiments, the first distance is sufficient to significantly reduce the light from the worker flames 118 that reaches the light detector 112 during operation. The light from the worker flames 118 may be due, in part, to the burning of hydrocarbons. The oxygen inlets 104 on the side of the conduit 102 are separated by a second distance that ranges from about 1 mm to about 20 mm. For example, in one embodiment, the second distance is 5 mm. The conduit 102 is shown with ten oxygen inlets 104, but one with ordinary skill in the art will appreciate that in other embodiments the apparatus may have as few as three oxygen inlets 104 or as many as ten or more.

In some embodiments the mFPD is capable of detecting sulfur at a concentration of less than $1 \times 10^{-10}$ g S/s during use.

In some embodiments the mFPD is capable of detecting phosphorus at a concentration of less than $1 \times 10^{-11}$ g P/s during use. In some embodiments the mFPD is capable of maintaining greater than 50% of its original analyte chemiluminescence even in the presence of up to 100 mL/min of hydrocarbon gas flow into the detector during use. During operation, the hydrocarbon gas flow may comprise aliphatic or aromatic hydrocarbons, for example, but not limited to methane, ethane, propane, butane, isobutane, pentane, hexane, benzene and toluene. In some embodiments, the apparatus may also include an igniter coupled to conduit 102.

In some embodiments, the apparatus may also be used to produce a linear response towards sulfur analytes, for example, through formation of the excited HSO* species. Conversion of sulfur analytes into this species may be most readily achieved through altering the gas flow to all of the worker flames (or any individual worker flame) to a more oxidizing atmosphere, for example, through increasing the oxygen (or air) flow to the worker flame(s) into the range of 30 to 200 mL/min based on the dimensions described.

FIG. 1B illustrates one embodiment of apparatus 100 that has a light detector 112. The detector is configured to detect light emissions that emanate through the detector port 108 and travel through light guide 132. The light detector 112 can be, for example, a photomultiplier tube or light detecting diode. The light detector 112 must be configured to convert photons into an electrical signal. The detector port 108 may be an opening in the conduit 102 or may be a window of a material that is transparent to the electromagnetic radiation being detected. For example, if the light detector is configured to detect visible light, the detector port 108 may be made of glass. The light guide 132 may be made of quartz or any material suitable to transmit light to the light detector 112.

A method for photometric detection is also presented. In some embodiments, the method comprises delivering an effluent gas 124, that includes an analyte, into a conduit 102.

Figure 8:
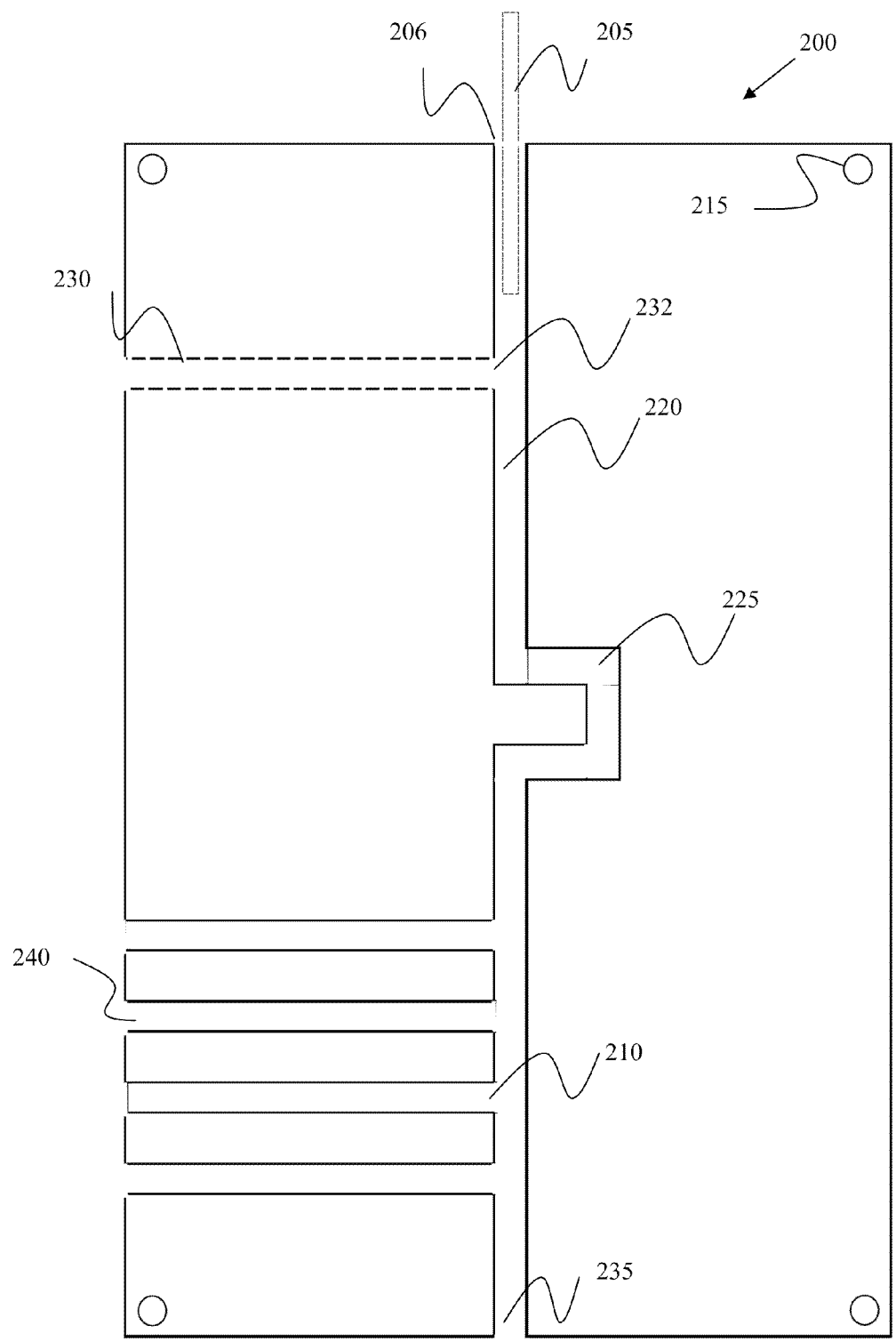
FIG. 8 is a schematic illustration of a component of a channel/chip-based mFPD apparatus for photometric detection. There is flexibility in this design. The top analytical flame, proximal to the distal end of oxygen tube 205, may be produced by conventional counter-current gas flow on, for example, a stainless steel capillary. The analytical flame may be produced "orthogonally," from the side, i.e., proximal to inlet 232. This figure is discussed in greater detail below.

FIG. 8 illustrates "chip-based" or "channel-based" embodiments of a component 200, which may be used as part of an apparatus for photometric detection. In some embodiments, some or all of component 200 may be made from the same material, e.g., stainless steel, glass, ceramic, silicon, or quartz. In some embodiments, it may be made using computerized milling, small drill bits, chemical based and/or laser-based etching techniques. In some embodiments, the channels, including conduit 220, as well as oxygen tubes 205 and 240 (pointing to just one of these), and/or optional oxygen tube 230, may be 0.5 to 1 mm wide channels.

Still referring to FIG. 8, component 200 has a conduit 220, which further comprises, three or more oxygen inlets 206 and 210 (pointing to just one of these), and/or optional oxygen inlet 232, and an analyte and hydrogen inlet 235. In this illustration, the top of the conduit is the distal end and the bottom of the conduit is the proximal end. In this embodiment, the final oxygen inlet 206 is at the top of the conduit and also serves as the effluent outlet during operation of the apparatus. In other embodiments, the final oxygen inlet and the effluent outlets are separate ports. For example, the final oxygen inlet may be orthogonal to the conduit, with 232 representing the final oxygen inlet and 206 representing the effluent outlet. In some embodiments, the apparatus may be configured to have the effluent outlet and final oxygen inlet be the same or different ports. This figure also shows the final oxygen inlet 206 coupled to an oxygen tube 205. In those embodiments where the final oxygen inlet is 232, it is coupled to oxygen tube 230.

Still referring to FIG. 8, the non-final oxygen inlets 210 are coupled to oxygen tubes 240. In some embodiments, one or more of the oxygen tubes 205, 230 and 240 may independently have the shape of a cylinder, a cuboid or a prism. In some embodiments, the cuboid is a rectangular box. In some embodiments, the cylinder is a circular cylinder, an elliptic cylinder, a parabolic cylinder, or a hyperbolic cylinders. In some embodiments, the cross section of one or more of the oxygen tubes 205, 230 and 240 has a semi-circular shape. In some embodiments, the cross section of one or more of the oxygen tubes 205, 230 and 240 has a shape as would result from an etching procedure. Additionally, the size and/or shape of one or more of the oxygen tubes 205, 230 and 240 may vary along their length. The tubes may be made of stainless steel, glass, quartz, ceramic, silicon or other materials. Each oxygen tube 205 and 240 has an inner diameter that ranges from about 0.05 mm to about 5 mm. In one example, the oxygen tubes have an inner diameter of about 0.25 mm. In some embodiments, each tube is in fluid connection with an oxygen source (not shown). During operation, the oxygen source may be used to support the combustion of the worker flames (not shown), which in this embodiment would be located in proximity to the oxygen inlets 210 (pointing to just one of these in FIG. 8). In some embodiments, the analytical flame (not shown) would be located in proximity to at the distal end of the oxygen tube 205 during operation. In other embodiments, the analytical flame (not shown) would be located in proximity to the optional final oxygen inlet 232. Regardless whether 206 or 232 is the final oxygen inlet, the analytical flame (not shown) would therefore be closer to the distal end of conduit 220 than the worker flames (also not shown).

Still referring to FIG. 8, the analyte and hydrogen inlet 235 is located at the proximal end of the conduit. During operation, effluent gas enters the conduit through the analyte and hydrogen inlet 235. In some embodiments, a hydrogen tube (not shown) enters through and/or is coupled to conduit 220 through analyte and hydrogen inlet 235. In other embodiments, the analyte inlet and the hydrogen inlet may be different ports. In some embodiments, the hydrogen tube (not shown) is configured to receive hydrogen gas from a hydrogen source (not shown). Effluent gas (not shown) flows from the proximal end of the conduit to the distal end of conduit 220. As the effluent gas travels through the conduit 220 during operation, it first comes into contact with the worker flames proximal to oxygen inlets 210, and then it comes into contact with the analytical flame proximal to optional final oxygen inlet 232 or to the proximal end of oxygen tube 205. It should be noted, however, that not all oxygen tubes 240 may have worker flames during operation. Some of the oxygen tubes 240 may be turned off or may not be connected to an oxygen source during operation. Bend 225 of conduit 220 is between the oxygen inlets 240 and final oxygen inlet 206 or 232 in the embodiments of this figure. During operations, bend 225 is in the flow path of the effluent, between the worker and analytical flames, thereby preventing light from the worker flames from bleeding into the analytical measurement. In the embodiments depicted in FIG. 8, this is accomplished with three 90 degree bends. In other embodiments, this can be accomplished with one, two, three or more bends or turns, each with angles ranging for 30 to 360 degrees.

Still referring to FIG. 8, component 200 may be constructed out of one or more of a variety materials, including quartz, glass, stainless steel, ceramic and silicon. In some embodiments, conduit 220 may be cylindrical in shape. In other embodiments, it may have the shape of a cuboid or a prism. In some embodiments, the cuboid is a rectangular box. In some embodiments, the cylinder is a circular cylinder, an elliptic cylinder, a parabolic cylinder, or a hyperbolic cylinders. In some embodiments, the cross section of some or all of the conduit 220 has a semi-circular shape. In some embodiments, the cross section of some or all of conduit 220 has a shape as would result from an etching procedure. In the embodiment of FIG. 8, the screw holes 215 (e.g., four shown in this embodiment) may be used to bolt down a cover of the same or similar dimension. In some embodiments such a cover may be bonded down. In some embodiments, it may be bonded and bolted down. Additionally, the size and/or shape of the conduit may vary along its length. For example, the conduit may be one size and/or shape in portions where the worker flames reside and another size and/or shape where a detector port (not shown) resides. In some embodiments, the conduit 220 has an inner diameter or an average inner diameter that ranges from about 0.1 mm to about 10 mm and a length from about 5 mm to about 1,000 mm. For example, in one embodiment, conduit 220 has an inner diameter or an average inner diameter of about 1 mm and a length of about 130 mm.

EXAMPLES

In one example, conduit 102 consists of a 130 mm length of a quartz tube (6 mm o.d.×1 mm i.d.) that is secured into the base of a GC instrument (Shimadzu model GC-8A) by a ¼ inch nut and Vespel ferrule. For exploration, the quartz tube has ten 1 mm oxygen inlets 104 drilled along one side that are spaced 5 mm apart starting at 50 mm from the bottom, or proximal end. Through each oxygen inlet 104, a 304 mm (12 inch) length of stainless steel (SS) oxygen tube (0.254 mm i.d.×0.4572 mm o.d.; Small Parts Inc., Miami Lakes, Fla., U.S.A.) is inserted and sealed (Resbond 940 cement; Cotronics Corp., Brooklyn, N.Y., U.S.A.) into place such that the end of the tube is flush with the inner wall of the conduit 102. High purity oxygen 116 (Praxair, Calgary, Canada) is delivered through these capillaries perpendicular to a high purity hydrogen 126 (Praxair) stream that is delivered up through the quartz from the base of the GC. The flames formed at the ends of these SS tubes are denoted 'worker' flames. A final typical counter-current flame is formed by inserting a SS oxygen tube 114 through the final oxygen inlet at the top of the conduit 102 and situating it 20 mm above the top worker flame. A photomultiplier tube (PMT; R-1104; Hamamatsu, Bridgewater, N.J., U.S.A.) monitors emissions from this flame, denoted the 'analytical' flame.

In one embodiment, the housing 130 consists of an 80 mm long SS cylinder (15 mm o.d.×1 mm wall thickness) with a 4 mm wide×75 mm long slit cut from the bottom, that slips over the protruding oxygen tubes 116. This extends downward to the ¼ inch nut of the detector port 108. A 7 mm×52 mm rectangular opening is cut into the cylinder 20 mm from the bottom to view the bottom worker flames 118 and an adjacent rectangular U-shaped piece of SS acts as a light-tight cover that slides over the opening as needed. One port of a ¼ inch Swagelok tee is welded to the top of the housing. One of the remaining ports is positioned opposite the analytical flame and connected to a length of ¼ inch SS tubing that contains a quartz light guide 132, which is used to direct emissions to the PMT 112. On the other port rests a SS cap that acts as a light tight conduit for the analytical flame. The cap consists of a ¼ inch Swagelok nut threaded onto a 20 mm cylinder with a tapered interior. The oxygen tube coupled to the final oxygen inlet is inserted through a rubber septum inside of this nut. In addition to protecting the PMT from stray light, this arrangement also helps exhaust flame gases and water formed by combustion. To view the analytical flame, a 4 mm hole is cut into the center of the tee. Similar to above, a smaller adjacent rectangular U-shaped piece of SS is also used to slide over and cover the hole as needed. Occasionally, heating tape is wrapped around the housing to assist in exhausting water build up as required. Further, while this design works very well, it should be noted that measurements may in other embodiments also be readily made in a dark adapted room without the housing and with the PMT situated directly opposite to the analytical flame. In either case, the sensitivity is found to be identical.

The flames are typically ignited according to the following sequence. With about 30 mL/min oxygen collectively flowing through the side capillaries and around 180 mL/min hydrogen flowing up through the quartz tube, a spark is presented at the tube surface and the nearest worker flame ignites. Next, the oxygen-bearing SS capillary (or tube) for the analytical flame is simply inserted into the top of the quartz, ignited at the first worker flame and then used to light each subsequent one. The analytical flame is then positioned next to the PMT window. This readily allows conversion between single, dual and multiple flame FPD modes. Unless otherwise specified, the hydrogen flow was normally near 100 mL/min, while the oxygen flows were around 7 mL/min for the analytical flame and 30 mL/min collectively across the worker flames.

Instrumentation and Supplies

Separations were performed on an EC-5 [(5%-phenyl-95%-methylpolysiloxane] megabore column (30 m×0.53 mm i.d.; 1.00 µm thickness; Alltech, Deerfield, Ill., U.S.A.) using direct splitless injection and high purity helium (Praxair) as the carrier gas at a flow rate of 5 mL/min. Standard analytes used for calibrations included tetrahydrothiophene (97%; Fluka Chemika, Oakville, Canada), trimethyl phosphite (97%; Aldrich, Oakville, Canada), decane (99%; BDH Lab Supplies, Toronto, Canada), and benzene (99%; Aldrich) dissolved in acetone (99.5%; EMD Chemicals, Gibbstown, N.J., U.S.A.) at varying concentrations. Methane (99%; Praxair) was used as a model hydrocarbon source in the quenching experiments. In examining response reproducibility a standard sulfur mixture was prepared, which consisted of dimethyl sulfide (99%; Aldrich), 2-propanethiol (97%, Aldrich), 1-methyl-1-propanethiol (99%; Aldrich), ethyl sulfide (99%; Aldrich), 1-butanethiol (99%; Aldrich), methyl disulfide (99%, Fluka Chemika), propyl sulfide (97%; Aldrich), isopropyl disulfide (97%; Aldrich), and ethyl disulfide (98%; Aldrich) in hexane (analytical reagent, BDH Lab Supplies) at various concentrations described in the text. Finally, as an application of the mFPD, some of these sulfur compounds were mixed in a range of volumetric ratios with pure gasoline that was purchased at a local vendor. The specific concentrations explored and any other variations are specified in the text.

Flame Configurations

Overall, a number of different configurations were explored in attempts to successfully create serial micro flames for use in detection. Initial efforts were related to the original micro counter-current flame design (Thurbide and Anderson, 2003; Thurbide and Hayward, 2004). In this way, the first prototypes had SS capillaries cemented into holes drilled directly opposite to one another along the side of the quartz tube. With one capillary (or tube) delivering hydrogen and the other oxygen, the characteristic counter-current flames were readily produced inside the quartz tube. However, these flames were unable to produce chemiluminescence for test analytes under a variety of conditions. This was attributed to analyte entering the flame in a stream of helium as opposed to hydrogen, as in a conventional FPD (Dressler, 1986; Thurbide et al., 2004). Subsequently, when hydrogen was also added to the helium effluent flow from the base of the GC, analyte chemiluminescence was improved but still relatively weak. Further, when attempting a dFPD arrangement this way with two micro counter-current flames in series, the stability and background emission of the lower oxygen-rich flame was problematic. Consequently, after several conditions were examined, hydrogen flow through the side ports was terminated and redirected to flow solely up through the quartz tube from the base of the GC. Interestingly, although a truly typical counter-current flow was not established, this now orthogonal gas flow scheme was found to also produce uniform, small, and stable flames upon each SS capillary that were similar to those observed originally (Thurbide and Anderson; 2003; Thurbide and Hayward, 2004). However, while this change promoted intense analyte chemiluminescence in all flames, the measured properties were poor due to the rather large background emission of these flames.

Ultimately, a conventional micro counter-current flame was additionally placed in series to the others, by directing another oxygen-bearing SS capillary through the top of the quartz tube. This produced a final flame that burned in a true counter-current stream of excess hydrogen. As well, this flame could be easily vertically positioned anywhere along the tube. Overall, due to the large background emission of the others, the best position for this flame was deemed to be near 20 mm above the lower flame, similar to a conventional dFPD (Patterson et al., 1978). As a result, when measuring emission in this flame, a very low background intensity and excellent analyte response was observed. Consequently, this upper flame was termed the 'analytical' flame, while the others below were termed 'worker' flames.

General Properties—Flame Characteristics and Appearance

In experimenting with this arrangement, it was found that essentially any number of worker flames could be constructed and introduced below the monitored analytical flame. Of note, 10 flames were operated in series without any difficulty in flame stability or ignition. Further, each flame appeared very uniform, compact in size, and visibly distinct from the others. While even greater flame numbers should also be readily obtained, these were not further explored as described later in the text. It should also be noted that peak broadening was not observed as a result of analyte travel through this multi-flame array. For example, when the column outlet was placed only 10 mm below the analytical flame (i.e. just above the worker flame array) test analyte injections yielded a peak base width of 7.6 seconds. Subsequently, when this was further tested 90 mm below the analytical flame (i.e. just below the worker flame array) the peak width was not observed to increase.

Figure 2:
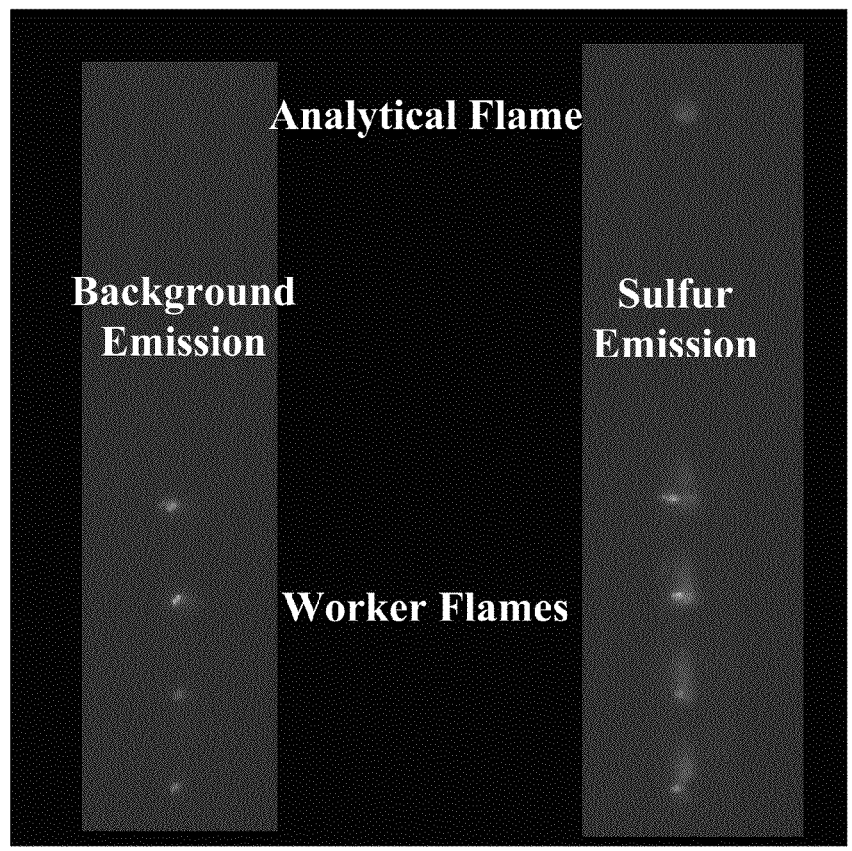
FIG. 2 depicts the flames of an mFPD under typical operating conditions. On the right, the effluent gas contains sulfur and one can see the chemiluminescence from the worker flames and the analytical flame. On the left, the effluent gas does not contain sulfur and one only sees the background emission from the worker flames.

FIG. 2 shows images of the mFPD with and without sulfur present under typical conditions. As seen in this example, 4 worker flames operate below the analytical flame. While their position is fixed, their appearance differs considerably in each trial. For example, in the absence of sulfur, the worker flame emission intensity is quite significant, likely due in part to incandescence from the cement used to hold the burners in place. By comparison, the analytical flame is substantially dim. However, when sulfur is present, the analytical flame displays the notable blue $S_2$ chemiluminescence characteristic of the conventional FPD (Dressler, 1986). Further, while the background emission of the worker flames remain intense in this case, a similar blue emission also surrounds each. Thus, clearly analyte degradation and excitation is occurring within each flame. Still, it should be noted that PMT measurements indicated that these worker flame emissions did not interfere in the analytical flame. As a result, the mFPD arrangement of FIGS. 1A & B was used as the primary burner configuration throughout the remaining experiments.

Resistance to Response Quenching—Quenching as a Function of Hydrocarbon Quantity Since the dFPD exhibits reduced response quenching, it was of interest to explore the properties of the mFPD in this regard. In order to best examine relative quenching effects, the single, dual, and multiple flame modes were each tested under similar conditions using methane as a model hydrocarbon. In each trial, a steady flow of methane was introduced at the bottom of the quartz tube where it combined with the hydrogen and column effluent from the base of the GC and flowed upward toward the analytical flame. There, the response from a test analyte was measured as various amounts of methane were introduced. Analyte response was then evaluated as a fraction of its original response obtained in the absence of methane.

Note that since analyte response and quenching resistance were found to be inversely impacted by the oxygen flow supplied to the worker flames, each mode examined was optimized for conditions that promoted both the best possible quenching resistance and analyte response. Also, since ideal conditions often occurred with equal oxygen flows at each worker flame, a uniform oxygen flow was delivered across all worker flames in subsequent experiments.

Figure 3:
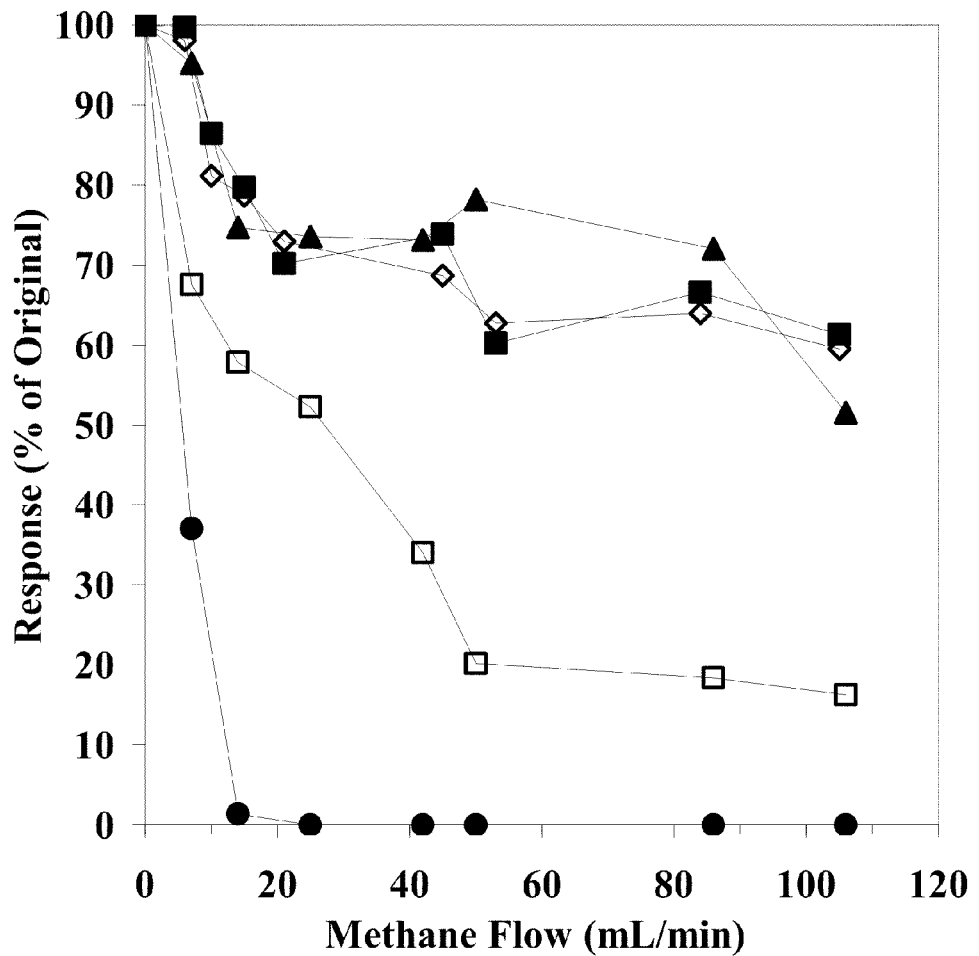
FIG. 3 is a response from a 1 µg injection of tetrahydrothiophene as a function of methane flow into the mFPD. Results are shown for one flame (●) [$H_2$ 75 mL/min]; two flames (□) [$H_2$ 75 mL/min; $O_2$ (worker) 9 mL/min]; three flames (▲) [$H_2$ 90 mL/min; $O_2$ (over 2 workers) 20 mL/min]; four flames (◇) [$H_2$ 75 mL/min; $O_2$ (over 3 workers) 24 mL/min]; and five flames (■) [$H_2$ 100 mL/min; $O_2$ (over 4 workers) 30 mL/min]. In each case the flame number includes the analytical flame and the worker flames. Oxygen flow to the analytical flame is 7 mL/min for each.

FIG. 3 shows typical results of these quenching investigations for sulfur emission and plots the fractional response from a 1 µg injection of tetrahydrothiophene as a function of methane flow into the detector. As observed in the single flame mode (i.e. without any worker flames) using hydrogen and oxygen flow rates near 75 and 7 mL/min respectively, sulfur response was reduced to 37% of its original value when just 7 mL/min of methane flowed into the flame. This was further reduced to 1.4% when 14 mL/min of methane was present (n.b. the optimal hydrogen flow of 40 mL/min reported previously for the µFPD (Thurbide and Hayward, 2004) produced similar results). As expected then, similar to a conventional FPD, quenching is a significant phenomenon in the single flame mode.

When one worker flame was added in series, analogous to a dFPD configuration, optimal conditions were found using 75 mL/min of hydrogen and oxygen flows near 7 mL/min in the analytical flame and 9 mL/min in the worker flame. However, in contrast to the single flame mode, sulfur response was reduced to about 58% of its original value in the presence of 14 mL/min of methane. Additionally, as the methane flows were increased toward extreme values of 50 and 100 mL/min, the sulfur response in this mode further reduced toward 16% of its original value. Therefore, similar to a conventional dFPD, this dual flame arrangement also shows improved quenching resistance relative to a single flame FPD.

Subsequently, when two worker flames were placed in series with the analytical flame, optimal conditions were found using around 90 mL/min of hydrogen and oxygen flows of about 7 mL/min in the analytical flame and 20 mL/min across the two worker flames (i.e., 10 mL/min each). In this mode, the quenching resistance was observed to further improve. For instance, at a methane flow of 14 mL/min, 75% of the original sulfur response is reasonably maintained. As well, in contrast to the single and dual flame scenarios, this response is sustained even as the methane flows increase toward extreme values around 100 mL/min.

Beyond this, a third and then a fourth worker flame were each also placed in series and tested. Accordingly, quenching resistance was also observed to further increase, but to less of an extent. For example, at about 14 mL/min of methane flow, three and four worker flames respectively maintained the sulfur response at 79 and 80% of its original value. However, in contrast to the dual flame mode, when three to five flames are placed in series, the sulfur response only reduced to about 60-65% when facing extreme methane flows near 100 mL/min.

Overall, improvements in performance appeared to taper off beyond the three flame mode, and little difference was seen in the quenching resistance between three flames and five. As such, additional worker flames were not similarly explored in this regard, and it was determined that the five flame mode was optimal for the quenching resistance observed. In this mode, optimal conditions were achieved using 100 mL/min of hydrogen and delivering oxygen flows of 7 mL/min to the analytical flame and 30 mL/min collectively to all four worker flames (i.e. 7.5 mL/min to each).

Resistance to Response Quenching—Comparison of Quenching in Single, Dual, and Multiple Flame Modes The results in FIG. 3 compare well with those presented earlier for the quenching of sulfur chemiluminescence. For example, in a conventional single flame FPD sulfur response was reduced by 50% in the presence of a methane flow corresponding to 43 µg C/s (~5 mL/min) (Aue and Sun, 1993). In comparison with the single flame trial of FIG. 3, the sulfur response was similarly reduced to 40% of its original value using a comparable flow of 7 mL/min of methane (~63 µg C/s). Additionally, the dFPD has been qualitatively shown to significantly improve quenching resistance relative to a single flame mode in direct comparisons (Patterson, 1978). As seen in FIG. 3, this is also clearly the case, since 25 mL/min of methane abolishes the single flame response, while the dual flame mode maintains about 50% of the original signal under these conditions.

Most interesting, however, FIG. 3 shows for the first time that operating more than two flames in series can significantly improve quenching resistance relative to an FPD and dFPD. For example, in the presence of 7 mL/min of methane (~63 µg C/s) the sulfur response is maintained at 95-100% of the original value when using three to five flames in series. Even more remarkable, sulfur response is still sustained at a level near 60% of the original value, even in the presence of enormous flows of methane around 105 mL/min (~945 µg C/s). Comparatively, the dual flame mode provides 16% of the original sulfur response under these extreme settings, while the single flame mode fails to provide any response. Overall then, using the 60% response level for a rough comparison, the multi flame mode appears to offer a nearly 10 fold improvement in quenching resistance relative to the dual flame mode. Relative to the single flame mode this likely amounts to more than a 20 fold improvement in the same.

Such a finding can be advantageous for mFPD analyses, particularly since the dFPD has been considered a quenching-free device for practical applications because it can accept 0.4 µg C/s without quenching (Kalontrov et al., 1995). Thus, compared to a dual flame mode, it can be anticipated that operation of multiple flames in the mFPD can afford the same or better quenching resistance in the presence of lower levels of hydrocarbons, such as those perhaps encountered in capillary column applications. Additionally, however, much better quenching resistance can also be anticipated from the mFPD in the presence of significantly greater amounts of hydrocarbons, such as those associated with packed columns or process streams.

Resistance to Response Quenching—Quenching as a Function of Analyte Mass

Since various results exist for FPD quenching effects as a function of analyte mass (Farwell and Barinaga, 1986; Dressler, 1986; Sugiyama et al., 1973), this aspect was also examined for the different mFPD modes. Table 2 compares the results for 10, 50, 100, 500, and 1000 ng injections of tetrahydrothiophene examined in the presence of increasing methane flows up to 25 mL/min for both the single and five flame mFPD modes. As seen, for the lower methane flow of 7 mL/min in the single flame mode, similar quenching resistance (~35% of original response remaining) is noted for masses of 100 ng or greater. However, for masses lower than this, complete quenching is observed. Consistent with FIG. 3, no response was observed for greater methane flows, regardless of the analyte mass injected. By comparison, for the 7 mL/min methane flow setting of the five flame trial, the smaller masses (50 and 10 ng) continue to elicit a sulfur response that is only slightly lower than the larger masses. Further, this pattern continues for higher methane flow rates of 14 and 25 mL/min. One notable exception, however, is that at the 25 mL/min setting the response toward 10 ng of analyte was completely quenched similar to the single flame trials employing 7 mL/min of methane. This finding is still reasonable considering that 25 mL/min of methane represents a tremendously large amount of hydrocarbon (~225 μg C/s) in the detector. In general then, as analyte mass decreases, analogous trends in quenching resistance are observed for the single and multi flame modes. However, it appears that the latter is much less impacted by comparison.

Table 2 summarizes quenching resistance data (% of original response) as a function of methane flow and tetrahydrothiophene in five flame and single flame modes.

TABLE 2

Quenching Resistance Data

| Analyte Mass | Single Flame Methane Flow 7 mL/min | Five Flames Methane Flow | | |
|---|---|---|---|---|
| | | 7 mL/min | 14 mL/min | 25 mL/min |
| 1.0 μg | 33.8 | 96.2 | 80.7 | 69.6 |
| 500 ng | 35.5 | 98.2 | 79.8 | 71.2 |
| 100 ng | 32.5 | 97.7 | 68.8 | 60.0 |
| 50 ng | 0 | 87.7 | 72.0 | 46.0 |
| 10 ng | 0 | 73.5 | 59.5 | 0 |

Resistance to Response Quenching—Rationalization for Quenching Resistance

In previous dFPD work, it has been reported that some designs convert hydrocarbons to carbon dioxide prior to entering the analytical flame (Rupprecht and Phillips, 1969), while others convert them mainly toward more reduced hydrogenated carbon species (Farwell and Barinaga, 1986; Patterson et al., 1978). To examine this aspect further in the mFPD, the setup was modified so that a FID response could be monitored in the analytical flame. This was accomplished by connecting the original FID electrical leads from the GC such that the polarizer was attached to the stainless steel capillary of the analytical flame, while a coiled collector was fashioned adjacent to it around the outlet of the quartz tube enclosing the flames. This configuration provided a sub-optimal but clearly detectable FID response from the analytical flame for a 10 μg injection of decane when none of the worker flames were ignited. However, when they were ignited under the exact same conditions, this same FID response completely disappeared. Since an FID does not respond to oxidized carbon (e.g., carbon dioxide) this finding strongly implies that the multi-flame modes of the mFPD are largely oxidizing the hydrocarbons, perhaps towards carbon dioxide formation, consistent with earlier dFPD findings (Rupprecht and Phillips, 1969). In terms of the quenching results displayed in FIG. 3, this finding is also reasonable considering the lack of FPD analyte response quenching that is observed in the presence of carbon dioxide, particularly when coupled to supercritical fluid chromatography using a carbon dioxide mobile phase (Olesik et al., 1989; Pekay and Olesik, 1989).

Finally, while the above quenching studies illustrate results obtained for sulfur response, it should be noted that phosphorus response quenching in the mFPD was also probed and yielded similar results. This agrees with others who showed the quenching behavior of numerous FPD-emitting species to be comparable (Aue and Sun, 1993). Still, since only sulfur and phosphorus response were explored here, similar extensions to other FPD-responding elements cannot be presently verified.

Optimization of Analyte Sensitivity—General Characteristics

An interesting observation was made in performing the quenching experiments. Initially, it was found that there was a notable decrease in the analyte signal when progressing from a single to a dual flame mode. In general, this was reasonable since decreased sensitivity has been observed in conventional dFPD designs (Rupprecht and Phillips, 1969; Patterson, 1978; Poole, 2003; Poole and Schuette, 1984; Ferguson and Luke, 1979; Tuan et al., 1994). Remarkably, however, as additional worker flames were added in series to the analytical flame, the analyte sensitivity was observed to readily recover and even surpass the original single flame values. This is interesting because sensitivity was so negatively impacted in the dual flame mode that the sulfur response could not be recovered under any condition examined. Conversely, the addition of multiple worker flames had such a positive impact on sensitivity that single flame response could not match the five flame mode levels under any condition examined. Therefore, the improvement in response appears to be a direct artifact of having three or more flames in series. As such, not only quenching resistance but also sensitivity seems to improve in the mFPD as flames are added.

In this regard, however, it must be reiterated that each of the different modes examined used conditions that were individually optimized to yield the best possible quenching resistance and analyte sensitivity. This is because oxygen flow in the worker flames had a significant influence on both. For example, in the dual flame mode of FIG. 3, quenching resistance could be increased to levels similar to those of the three to five flame modes. Of note, about 30 mL/min of oxygen to the worker flame(s) in any mode appeared to yield maximum quenching resistance in the mFPD. However, under these conditions the dual flame mode sensitivity was found to dramatically drop by an order of magnitude or more, due to the unique opposing effect of the worker flame on quenching resistance and sensitivity in this mode.

Optimization of Analyte Sensitivity—Analyte Sensitivity as a Function of Worker Flames To better illustrate this phenomenon, an experiment was performed where absolute analyte response was measured in the analytical flame solely as a function of the number of worker flames beneath it. As such, efforts were made to keep all other conditions as constant as possible. To this end, the analytical flame was held at optimal conditions of 7 mL/min of oxygen and 40 mL/min of hydrogen in each trial. Additionally, the total worker flame oxygen flow (i.e., collectively over all worker flames) was maintained at 30 mL/min, where maximum quenching resistance was noted earlier. Accordingly then, the overall hydrogen flow was set to 100 mL/min in order for the stoichiometric excess to provide the optimal 40 mL/min of hydrogen to the analytical flame. The results of this experiment are presented in Table 3 for both sulfur and phosphorus analytes.

As can be seen, in the single flame mode, injections of tetrahydrothiophene and trimethyl phosphite produce respective signals of 237 and 128 mV. However, when a single worker flame is introduced en-route to a dual flame mode, these signals diminish by an order of magnitude. When a third flame is added, the signals recover to about 70% of their original value. When a $4^{th}$ flame is added, the signals then surpass the originals. A $5^{th}$ flame then continues this trend. Consequently, 6 to 10 flames were also explored, but this began to erode the gains realized. Therefore, not only is maximum quenching resistance obtained with a worker flame oxygen flow rate of 30 mL/min, but the sensitivity is optimal when this flow is placed across 4 worker flames beneath the analytical flame. As such, the results in Table 3 demonstrate that even though the sensitivity does significantly reduce when progressing from the single to dual flame mode, it can be recovered and even enhanced when more flames are placed in series, without compromising the quenching resistance of the mFPD.

It is uncertain as to why this occurs, however it appears likely that the elevated oxygen flow at the single worker flame in the dual flame mode negatively impacts the hydrogen-rich environment used to promote analyte chemiluminescence at the analytical flame (Dressler, 1986). In this way, it is interesting to note that with four worker flames the oxygen flow through each capillary (near 7.5 mL/min) is roughly equal to that of the analytical flame, which suggests that this amount of oxygen may provide optimum conditions at each burner. However, spectroscopic investigations of each flame would be required to confirm this. Nonetheless, these results clearly indicate the optimal mFPD arrangement to be five flames placed in series (i.e., 4 workers and 1 analytical).

Analytical Figures of Merit—Detection Limit and Response Range

In terms of the detector noise observed, little difference was noted between the single and five flame mFPD modes. However, the dual flame mode often displayed relatively larger noise. For instance, in the trials of Table 3 this difference amounted to an order of magnitude and is likely due to the larger oxygen flow directed through the single worker flame. Therefore, to further explore this, the photometric response toward various masses of sulfur and phosphorus analytes were calibrated with respect to the detector noise in different mFPD modes.

Figure 4:
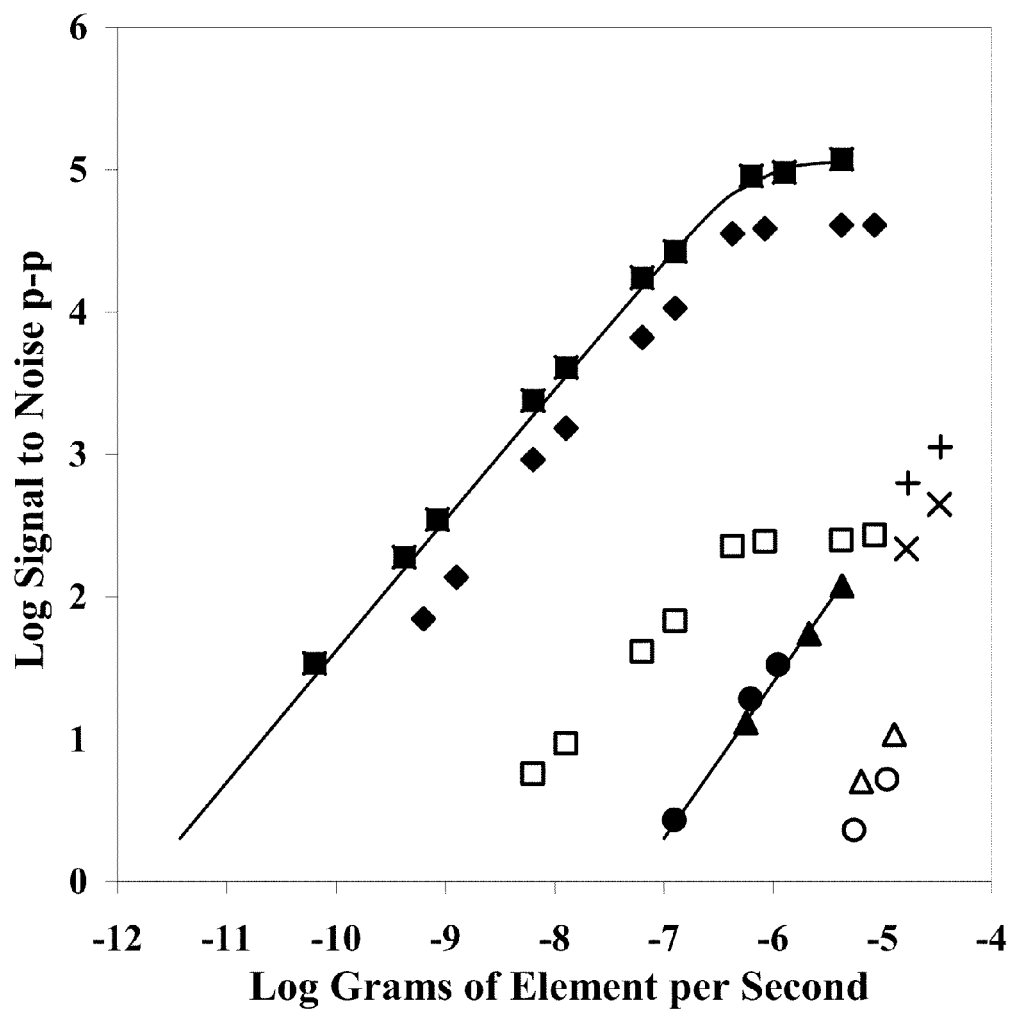
FIG. 4 shows typical mFPD calibration curves for trimethyl phosphite in the single (♦), dual (□), and five (■) flame modes; decane in the single (X), dual (○), and five (●) flame modes; and benzene in the single (+), dual (Δ), and five flame (▲) modes. Conditions are the same as those used in Table 3.

FIG. 4 illustrates these efforts with the typical calibration curves obtained for trimethyl phosphite in the mFPD, operating under the optimized conditions summarized in Table 3. As can be observed, phosphorus response (plotted as signal over peak to peak noise) is initially strong in the single flame mode. Subsequently, as expected from Table 3 and conventional dFPD behavior (Rupprecht and Phillips, 1969; Patterson, 1978; Poole, 2003; Poole and Schuette, 1984; Ferguson and Luke, 1979; Tuan et al., 1994), it then diminishes by nearly two orders of magnitude when operating in the dual flame mode, as a result of the negative impact on both signal and noise. However, when progressing to the optimal five flame mode, the mFPD response then recovers to a level slightly better than that of the single flame mode, also consistent with the results of Table 3. Under these conditions, phosphorus emission in the mFPD yields a linear response over 5 orders of magnitude with a minimum detectable limit (MDL) of about $3 \times 10^{-12}$ gP/s. The latter was determined at a signal-to-noise ratio of 2, where noise was measured as the peak to peak baseline fluctuations over at least 10 analyte peak base widths. The sulfur response in the various mFPD modes also changed in a similar fashion to that shown in FIG. 4. Consequently, in the five flame mode, sulfur response is quadratic over 4 orders of magnitude with a MDL of around $4 \times 10^{-11}$ gS/s. Overall then, these values agree very well with those expected from a conventional FPD (Dressler, 1986). However, unlike a conventional FPD but similar to earlier dFPD designs (Patterson et al., 1978; Patterson, 1978), it should be noted that sulfur and phosphorus response in the mFPD also share the same optimal gas flow rates. As noted above, in some embodiments, the apparatus may also be used to produce a linear response towards sulfur analytes, for example, through formation of the excited HSO* species. Conversion of sulfur analytes into this species may be most readily achieved through altering the gas flow to all of the worker flames (or any individual worker flame) to a more oxidizing atmosphere, for example, through increasing the oxygen (or air) flow to the worker flame(s) into the range of 30 to 200 mL/min based on the dimensions described.

Table 3 shows mFPD response toward 1 µg injections of tetrahydrothiophene and trimethyl phosphite as a function of the number of worker flames. Oxygen flow rates were 7 mL/min(analytical flame) and 30 mL/min total (across all worker flames). Hydrogen flow was 100 mL/min, except for the single flame mode where it was 40 mL/min.

TABLE 3 mFPD Response to Tetrahydrothiophene and Trimethylphosphite

| Mode | Sulfur Response (mV) | Phosphorus Response (mV) |
|---|---|---|
| 1-Flame (analytical) | 237 | 128 |
| 2-Flames (1-analytical; 1-worker) | 22 | 15 |
| 3-Flames (1-analytical; 2-workers) | 166 | 92 |
| 4-Flames (1-analytical; 3-workers) | 354 | 229 |
| 5-Flames (1-analytical; 4-workers) | 744 | 510 |
| 6-Flames (1-analytical; 5-workers) | 576 | 483 |
| 10-Flames (1-analytical; 9-workers) | 475 | 406 |

Analytical Figures of Merit—Analyte Response Selectivity Over Hydrocarbons

Also included in FIG. 4 is an evaluation of carbon response in the various mFPD modes examined. As can be seen, the changes in carbon response are similar to those of phosphorus and sulfur response in the different modes. In the single flame mode both decane and benzene yield distinctly different responses in terms of carbon flow into the detector. This agrees with previous FPD studies of carbon response (Thurbide, K. B.; Hayward, 2004; Sun et al., 1992). However, in the dual flame mode, these compounds elicit more similar levels of response. This suggests that as these aliphatic and aromatic compounds pass through the worker flame they degrade and homogenize into similar (perhaps oxidized) species, prior to entering the analytical flame. Consequently, in the five flame mode, this trend continues as the response returns to near the original level of the single flame mode.

It should be emphasized that the data in FIG. 4 were obtained in the open unfiltered mode, and therefore they represent the native sensitivity and selectivity available in the mFPD. In this regard, phosphorus in the five flame mFPD mode yields a molar selectivity over carbon (i.e. mol P/mol C that yield the same response within the linear range) of nearly 5 orders of magnitude. Conversely, the quadratic response of sulfur in this mode yields a molar selectivity over carbon of around 3.5 orders of magnitude at the lower concentration range. Again, these mFPD values also agree with those of a conventional FPD (Dressler, 1986). Additionally, since it is common practice to use wavelength specific interference filters to increase selectivity in the conventional FPD, these were also examined in the mFPD and were found to improve selectivity over carbon as expected. Of note, when monitoring sulfur response at 393 nm and phosphorus response at 520 nm in the five flame mode, no signals were observed for any injected amounts of decane or benzene examined upward to 100 μg. Therefore, no major interferences are anticipated in the ability to selectively monitor phosphorus or sulfur-containing analytes in the mFPD.

Reproducibility and Equimolarity of Sulfur Response

As mentioned earlier, variations in the FPD response toward sulfur containing compounds of differing molecular structure have been noted over the years (Sugiyama et al., 1973; Burnett et al., 1978; Hayward and Thurbide, 2006). Therefore this aspect was investigated more closely in the mFPD. In particular, the reproducibility and response equimolarity in several modes of mFPD operation were explored for a range of nine different organic sulfur compounds. The mixture of analytes was examined in 10 consecutive trials where the reproducibility of sulfur response for each was determined by measuring the peak areas produced and then calculating the % RSD of the average value. As well, the response equimolarity was also probed by then using the average peak area for each analyte to determine the corresponding response per mole of sulfur introduced. These figures were then normalized by treating the median value as unity. Table 4 summarizes reproducibility and equimolarity of response for a nine component sulfur mixture in the single, dual, and five flame modes of the mFPD. The GC temperature program used was 30° C. for 2 minutes initially and then increased by 32° C./min to 130° C.

TABLE 4

Reproducibility and Equimolarity Data

| | % RSD | | | Response Equimolarity | | |
|---|---|---|---|---|---|---|
| Compound | Single Flame | Dual Flame | Five Flames | Single Flame | Dual Flame | Five Flames |
| Dimethyl sulfide | 8.0 | 10.3 | 6.7 | 1.4 | 1.2 | 1.1 |
| 2-Propanethiol | 9.9 | 11.2 | 4.9 | 0.7 | 0.4 | 0.9 |
| 1-Methyl-1-propanethiol | 7.9 | 9.6 | 5.0 | 1.0 | 1.0 | 1.2 |
| Ethyl sulfide | 8.3 | 9.9 | 5.3 | 1.0 | 1.0 | 0.9 |
| 1-Butanethiol | 7.3 | 7.9 | 4.7 | 1.0 | 0.9 | 0.8 |
| Methyl disulfide | 6.7 | 9.7 | 4.2 | 1.8 | 1.0 | 1.0 |
| Propyl sulfide | 7.4 | 11.1 | 4.3 | 0.6 | 1.2 | 1.0 |
| Isopropyl disulfide | 11.4 | 12.1 | 7.2 | 1.7 | 1.8 | 1.4 |
| Ethyl disulfide | 9.0 | 7.3 | 4.1 | 0.7 | 0.9 | 1.1 |

As seen, in terms of reproducibility, the single flame mode displays % RSD values ranging from 6.7 to 11.4, with an average of 8.4% over all of the analytes. These findings agree very well with earlier experiments that established similar sulfur response characteristics between this mode and a conventional FPD (Hayward and Thurbide, 2006). Comparable results were also obtained in the dual flame mode, which produced % RSD values ranging from 7.3 to 12.1, with an average of 9.9% for the same analytes. In contrast to this, however, the five flame mFPD mode yielded noticeably smaller % RSD values ranging from 4.1 to 7.2, with an average of 5.1% for the mixture.

Regarding response equimolarity, data from the single flame mode produces normalized response per mole values ranging from 0.6 to 1.8 for the compounds examined. Of these, three of nine analytes have values within ±0.2 of unity. This is somewhat expected since the FPD is not generally known to provide a relatively uniform response factor for various sulfur analytes (Hayward and Thurbide, 2006). However, the situation improves when proceeding to the dual flame mode, which produces values ranging from 0.4 to 1.8, where seven of nine compounds are within ±0.2 of unity and five are within ±0.1. This is consistent with the greater response uniformity that has been noted previously for the dFPD (Poole, 2003). By comparison though, the five flame mFPD mode appears to further improve response equimolarity by producing values ranging from 0.8 to 1.4. Further, eight of the nine values are within ±0.2 of unity, while six are within ±0.1.

Overall then, these results confirm earlier findings that a dFPD can provide a more uniform sulfur response over a range of analytes of varying molecular structure. However, they additionally suggest that this effect is further improved and that analyte response is more reproducible in the five flame mode of the mFPD compared to the single and dual flame modes. Therefore, this implies that multiple flames facilitate the consistent provision of a homogenous $S_2$-containing effluent to the analytical flame, more so than the other modes of operation.

Analysis of Sulfur Compounds in Gasolines

To better probe its analytical characteristics in a practical application, the mFPD was used to detect sulfur analytes amongst various hydrocarbons present in commercial gasoline. Specifically, six sulfur compounds were mixed with various volumes of pure gasoline and then analyzed using both the single flame and the five flame mFPD modes. To do so, five solutions of the same volume were prepared such that each contained the same amount of sulfur analytes (~1 μg of each) in hexane, but with an increasing volume fraction (from 0 to 80%) of gasoline. The results of these experiments are displayed in FIGS. 5 and 6.

Figure 5:
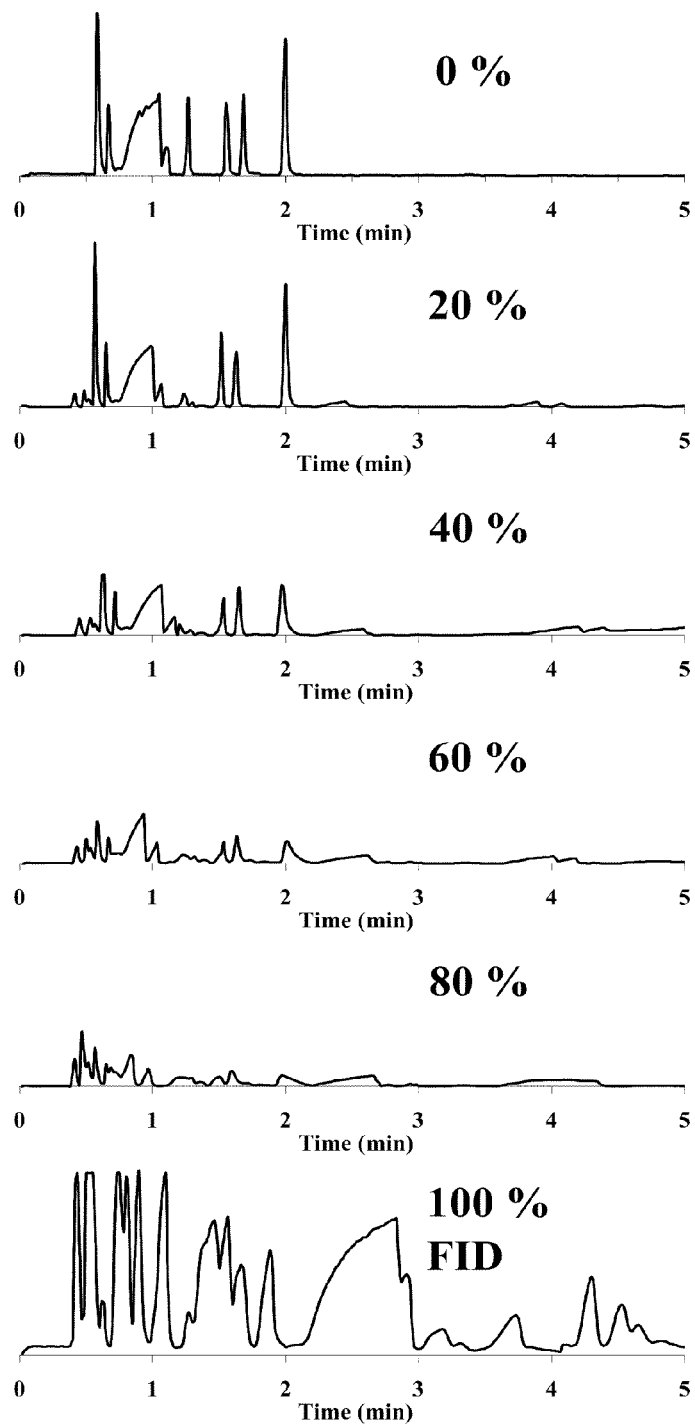
FIG. 5 shows single flame mFPD chromatograms of six sulfur compounds (~1 μg each in hexane) mixed with increasing volume percentages of gasoline. The bottom chromatogram shows an Flame Ionization Detector (FID) trace of the pure gasoline. The temperature program used was 30° C. for 3 minutes, then immediately increasing to 250° C. for 5 minutes. The analyte elution order is dimethyl sulfide, 2-propanethiol, (solvent peak), 1-methyl-1-propanethiol, ethyl sulfide, 1-butanethiol, and methyl disulfide.

As seen from the single flame trials of FIG. 5, when 0% gasoline is present in the sample matrix, six well defined sulfur peaks can be easily identified amongst the hexane solvent peak that is also present. However, when the solution contains 20% gasoline, the peak for 1-methyl-1-propanethiol near 1.25 minutes is effectively completely quenched. When 40% gasoline is present, all of the sulfur analytes exhibit noticeable quenching. Finally, when 60% and 80% gasoline are respectively present, the signals are essentially destroyed. This response quenching is a direct result of the overlap of these analytes with the various hydrocarbon components present in the gasoline sample. For instance, the bottom chromatogram of FIG. 5 (and FIG. 6 for consistency) shows an FID trace of the pure gasoline sample, which demonstrates that most of the hydrocarbons elute between 0.5 and 3 minutes where they severely overlap with the retention times of the sulfur standards.

Figure 6:
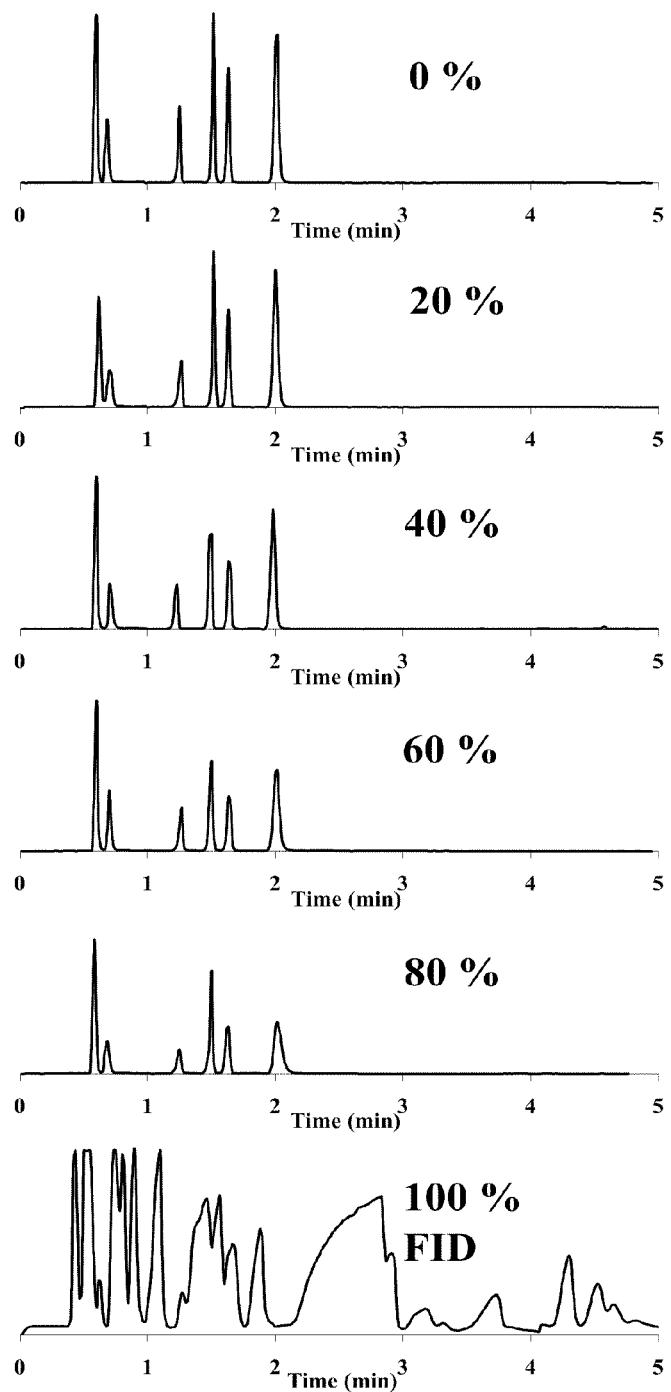
FIG. 6 shows five flame mFPD chromatograms of six sulfur compounds (~1 μg each in hexane) mixed with increasing volume percentages of gasoline. The bottom chromatogram shows an FID trace of the pure gasoline. Conditions and analytes are the same as in FIG. 5.

In contrast to this, FIG. 6 demonstrates the same experiment when using the five flame mode of the mFPD. In this case, strong clear analyte signals remain throughout each trial. Of note, very good and well defined sulfur peaks are still detected in this mFPD mode even at the 80% v/v level, where a very large amount of gasoline is present in the sample. Considering that the same hydrocarbon quantities and degree of analyte overlap exist between the experiments in FIGS. 5 and 6, this greatly improved performance can be directly attributed to the favorable quenching resistance and analyte sensitivity displayed by the five flame mFPD mode. Therefore, this demonstrates that the mFPD can be beneficial in such applications where these parameters may otherwise be compromised.

In the five flame trials of FIG. 6, the interfering hydrocarbon response from the hexane solvent peak and the gasoline component peaks is significantly reduced compared to the single flame mode of FIG. 5. This further demonstrates the notable improvement in analyte selectivity over carbon in the mFPD. However, since FIGS. 5 and 6 were obtained in the absence of an interference filter, this also represents the difference in native selectivity for these modes. Thus, although it would further reduce sensitivity, it is likely that the single flame hydrocarbon signals shown in FIG. 5 may be diminished by using an appropriate filter. By comparison though, it is also useful to note that the five flame mFPD mode does not appear to require this under the conditions examined.

Figure 7:
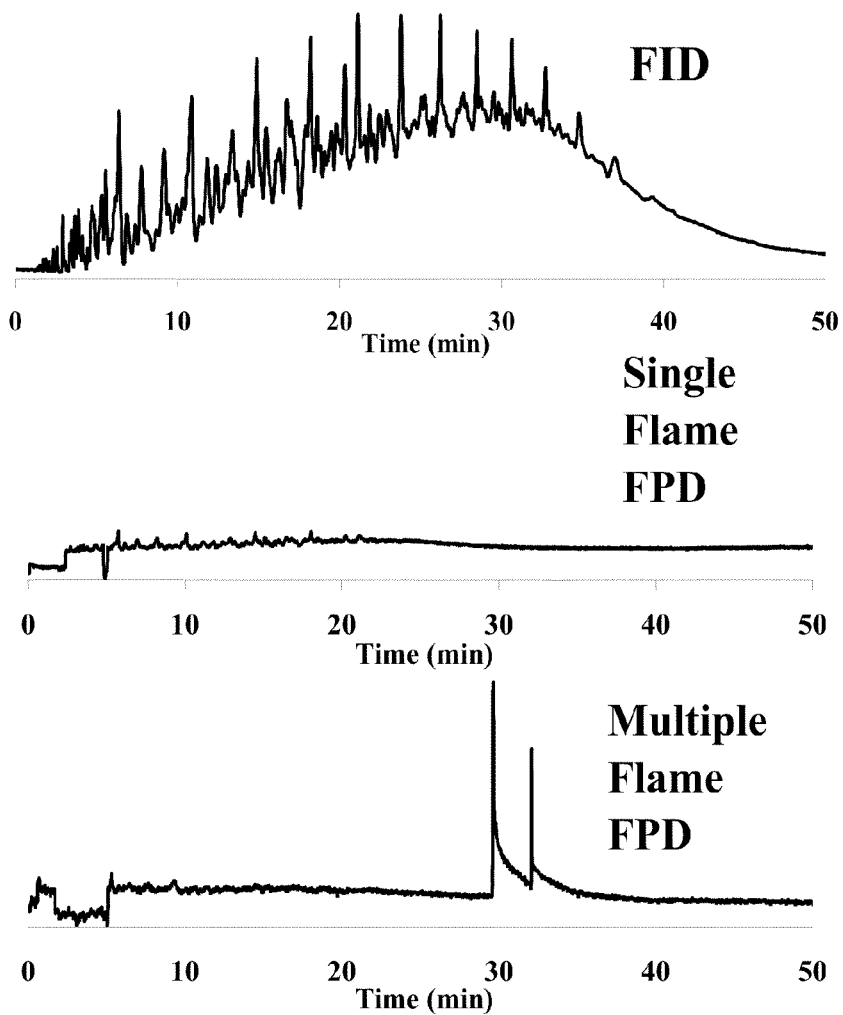
FIG. 7 shows a GC analysis of a commercial diesel fuel by FID (upper trace), single flame FPD (middle trace), and five flame mFPD (lower trace). Flame conditions are the same as those used in Table 3. The temperature program in each separation is 70° C. initial for 5 minutes, then increased to 280° C. at 5° C./minute (EC-5 capillary column, 50 m×0.53 mm i.d.). Each FPD trial uses a 393 nm interference filter.

FIG. 7 demonstrates the direct GC analysis of a commercial diesel fuel using FID, single flame FPD, and five flame mFPD detection modes for comparison. As seen in the FID trace, a very large number of unresolved hydrocarbon components continually elute during the 50 minute separation. When monitored at 393 nm in the single flame FPD mode, however, no peaks are effectively observed. Conversely, when this is also done in the five flame mFPD mode, the same separation reveals at least two major sulfur species. Comparison with standards and GC-MS analysis of this sample indicates that these are dibenzothiophene and its 1-methyl analogue. Thus, it appears that severe hydrocarbon quenching prevents the conventional single flame FPD from detecting these sulfur analytes, whereas the five flame mFPD mode is capable of sensing them within the exact same matrix. Clearly, further optimization of the separation conditions could improve any peak tailing observed and potentially reveal other species present. Nonetheless, it is significant that the mFPD readily detected these analytes after simply purchasing the diesel fuel at a local vendor and injecting a pure 1 µL volume of it for analysis.

In closing, it is worth mentioning that the detector time constant of the five flame mFPD mode is very similar to that of the conventional single flame mode. In fact, measurements performed with each indicate these values to be in the low millisecond range. As such, the mFPD should be a suitable detector for more rapid separation methods invoking fast GC. In fact, the latter has already been demonstrated with the single flame µFPD mode (Kendler et al., 2006). Additionally, it should be noted that the mFPD has been observed to be a very rugged device that provides reliable stable operation and excellent day to day method reproducibility. It is also reasonably simple to operate and it has been found that students can be trained to work independently with the device in a very short period. As such, new users should find the mFPD to be fairly adaptable for their purposes.

References

The following references, to the extent that they provide exemplary procedural or other details supplementary to those set forth herein, are specifically incorporated herein by reference.

Aue and Sun, *Chromatogr.*, 633:151-162, 1993.
Aue and Sun, *J. Chromatogr.*, 641:291-299, 1993.
Baruah and Khare, *Energy and Fuels*, 21:3346-3352, 2007.
Brody and Chaney, *J. Gas Chromatogr.*, 4:42-46, 1966.
Burnett et al., *J. Chromaotgr. Sci.*, 16:68-73, 1978.
Chen et al., *Food Chemistry*, 112:956-961, 2008.
Cheskis et al., *Anal. Chem.*, 65:539-555, 1993.
Clay et al., *Anal. Chem.*, 49:126-128, 1977.
Dressler, In: *Selective Gas Chromatographic Detectors*; Elsevier: Amsterdam, 152-156, 1986.
Farwell and Barinaga, *J. Chromatogr. Sci.*, 24:483-494, 1986.
Ferguson and Luke, *Chromatographia*, 12:197-203, 1979.
Fuentes et al., *J. Chromatogr. A.*, 1207:38-45, 2008.
Hayward and Thurbide, *J. Chromatogr. A*, 1105:66-70, 2006.
Hayward and Thurbide, *J. Chromatogr. A*, 1200:2-7, 2008.
Hayward and Thurbide, *Talanta*, 73:583-588, 2007.
Kalontrov et al., *J. Chromatogr. A*, 696:245-256, 1995.
Kendler et al., *Anal. Chem.*, 78:6765-73, 2006.
Kendler et al., *Anal. Chim. Acta*, 548:58-65, 2005.
Koizumi and Suzuki, *Anal. Sci.*, 7:241-244, 1991.
Li et al., *J. Sep. Sci.*, 31:3588-3594, 2008.
Logan et al., *Toxicology Mechan. Methods*, 16:359-363, 2006.
Machino, *Sekiyu Gakkaishi*, 39:370-373, 1996.
McGuffin and Novotny, *Anal. Chem.*, 53:946-951, 1981.
Olesik et al., *Anal. Chem.*, 61:58-65, 1989.
Patterson et al., *Anal. Chem.*, 50:339-344, 1978.
Patterson, *Anal. Chem.*, 50:345-348, 1978.
Pearson and Hines, *Anal. Chem.*, 49:123-126, 1977.
Pekay and Olesik, *Anal. Chem.*, 61:58-65, 1989.
Poole and Schuette, In: *Contemporary practice of chromatography*, Elsevier: Amsterdam, 187, 1984.
Poole, In: *The essence of chromatography*; Elsevier: Amsterdam, 247, 2003.
Rupprecht and Phillips, *Anal. Chim. Acta*, 47:439-449, 1969.
Seto et al., *Toxin Reviews*, 26:299-312, 2007.
Sevcik and Thao, *Chromatographia*, 8:559-162, 1975.
Sugiyama et al., *J. Chromatogr.*, 77:309-316, 1973.
Sugiyama et al., *J. Chromatogr.*, 80:61-67, 1973.
Sun et al., *Can. J. Chem.*, 70:1129-1142, 1992.
Thurbide and Anderson, *Analyst*, 128:3-8, 2003.
Thurbide and Aue, *J. Chromatogr. A*, 694:433-440, 1995.
Thurbide and Hayward, *Anal. Chim. Acta*, 519:121-128, 2004.
Thurbide et al., *J. Chromatogr. A*, 1029:193-203, 2004.
Tolosa et al., *Fresenius J. Analy. Chem.*, 339:646-653, 1991.
Tuan et al., *J. High Resol. Chromatogr.*, 17:373-389, 1994.
Wang et al., *Ind. Eng. Chem. Res.*, 48:142-147, 2009.
Zhao et al., *Energy Fuels*, 22:1100-1103, 2008.

What is claimed is:

1. A quenching resistant multiple flame photometric detector (mFPD), comprising
   (a) a conduit comprising a proximal and a distal end, and also comprising:
      (1) an analyte inlet positioned at the proximal end of the conduit providing for a flow of analyte towards a worker flame region;
      (2) a hydrogen inlet positioned at the proximal end of the conduit;
      (3) a worker flame region comprising at least a first and second work flame in fluid connection with at least a first and a second oxygen inlet positioned between the proximal and distal ends of the conduit providing for flow of oxygen towards said first and second worker flames;
      (4) a final oxygen inlet at the distal end of the conduit providing a flow of oxygen towards an analytical flame;
      (5) a detector port positioned at the distal end of the conduit; and
   (b) a light detector configured to detect emissions passing out through the detector port.

2. The mFPD of claim 1, where each oxygen inlet is coupled to an oxygen tube.

3. The mFPD of claim 2, where each oxygen tube is in fluid connection with one or more oxygen sources.

4. The mFPD of claim 3, where the final oxygen inlet is nearest to a distal end of the conduit, the first oxygen inlet is nearest to a proximal end of the conduit, and the second oxygen inlet is located between the first oxygen inlet and the final oxygen inlet.

5. The mFPD of claim 4, where the final oxygen inlet is separated from the second oxygen inlet by a first distance of about 2 mm to about 50 mm.

6. The mFPD of claim 5, where the first distance is about 20 mm.

7. The mFPD of claim 5, where the second oxygen inlet is separated from the first oxygen inlet by a second distance of about 1 mm to about 20 mm.

8. The mFPD of claim 7, where the second distance is about 5 mm.

9. The mFPD of claim 2, where one or more of the oxygen tubes is a stainless steel tube.

10. The mFPD of claim 2, where the conduit and one or more of the oxygen tubes are made from the same material.

11. The mFPD of claim 5, where the conduit and one or more of the oxygen tubes are comprised from a unitary piece.

12. The mFPD of claim 6, where the material is stainless steel.

13. The mFPD of claim 6, where the material is quartz.

14. The mFPD of claim 2, where the conduit and one or more of the oxygen tubes are separate components.

15. The mFPD of claim 2, where each oxygen tube has an inner diameter from about 0.05 mm to about 5 mm.

16. The mFPD of claim 10, where the inner diameter of each oxygen tube is about 0.25 mm.

17. The mFPD of claim 2, where at least three flames reside each at an end of a respective oxygen tube during use.

18. The mFPD of claim 12, where the size of one or more of the flames is between about 3 nL to about 1 mL.

19. The mFPD of claim 13, where the size of one or more of the flames is about 30 nL.

20. The mFPD of claim 12, where the cross section of one or more of the flames through its center occupies from 50% to 95% of the cross section of the conduit.

21. The mFPD of claim 15, where the cross section of one or more of the flames through its center occupies from 60% to 85% of the cross section of the conduit.

22. The mFPD of claim 16, where the cross section of one or more of the flames through its center occupies about 75% of the cross section of the conduit.

23. The mFPD of claim 1, where there are one or more bends in the conduit between the final oxygen inlet and the next closest oxygen inlet along the length of the conduit.

24. The mFPD of claim 23, wherein each bend has an angle from 30 to 360 degrees.

25. The mFPD of claim 24, where there are three 90 degree bends in the conduit between the final oxygen inlet and the next closest oxygen inlet along the length of the conduit.

26. The mFPD of claim 1, where the conduit is quartz, glass, stainless steel, ceramic or silicon.

27. The mFPD of claim 1, wherein the shape of some or all of the conduit is that of a circular cylinder, an elliptic cylinder, a parabolic cylinder, or a hyperbolic cylinder.

28. The mFPD of claim 27, where the conduit has at least one inner diameter from about 0.1 mm to about 10 mm.

29. The mFPD of claim 28, where the conduit is a circular cylinder and the inner diameter of the conduit is about 1 mm.

30. The mFPD of claim 27, where the conduit has a length from about 5 mm to about 1,000 mm.

31. The mFPD of claim 30, where the length is about 130 mm.

32. The mFPD of claim 1, wherein the cross section of some or all of the conduit has a semi-circular shape.

33. The mFPD of claim 1, wherein the cross section of some or all of the conduit has a shape as would result from an etching procedure.

34. The mFPD of claim 1, where the conduit comprises:
i) a first oxygen inlet,
ii) a second oxygen inlet,
iii) a third oxygen inlet, and
iv) a final oxygen inlet.

35. The mFPD of claim 1, where the conduit comprises:
i) a first oxygen inlet,
ii) a second oxygen inlet,
iii) a third oxygen inlet,
iv) a fourth oxygen inlet, and
v) a final oxygen inlet.

36. The mFPD of claim 1, where the conduit comprises:
i) a first oxygen inlet,
ii) a second oxygen inlet,
iii) a third oxygen inlet,
iv) a fourth oxygen inlet,
v) a fifth oxygen inlet, and
vi) a final oxygen inlet.

37. The mFPD of claim 1, where the hydrogen inlet is in fluid connection with a hydrogen source, the oxygen inlets are in fluid connection with one or more oxygen sources, and the analyte inlet is in fluid connection with the analyte source.

38. The mFPD of claim 37, where the hydrogen inlet is positioned closer to the proximal end of the conduit than the oxygen inlets.

39. The mFPD of claim 37, where the analyte inlet is positioned closer to the proximal end of the conduit than the oxygen inlets.

40. The mFPD of claim 1, further comprising an igniter coupled to the conduit.

41. A method of detecting analyte using a quenching resistant multiple flame photometric detector (mFPD), comprising:
(1) delivering an effluent comprising analyte into a conduit comprising a proximal end and a distal through an analyte inlet and, said conduit also comprising:
(a) a worker flame region comprising:
i) a first oxygen inlet,
ii) a second oxygen inlet, and
iii) a final oxygen inlet;
where the final oxygen inlet is closest to the distal end of the conduit, the first oxygen inlet is closest to the proximal end of the conduit and the second oxygen inlet is located between the first oxygen inlet and the final oxygen inlet;
where the oxygen inlets are coupled to oxygen tubes in fluid connection with an oxygen source;
where an analytical flame resides at the tube coupled to the final oxygen inlet and worker flames reside at the tubes coupled to the first oxygen inlet and the second oxygen inlet;
(b) a hydrogen inlet positioned at the proximal end of the conduit being in fluid connection with a hydrogen source and providing for a flow of hydrogen towards the work flame region;
(c) a detector port positioned at the distal end of the conduit; and
(d) an analyte inlet positioned at the proximal end of the conduit through which an effluent is delivered;
(2) contacting the effluent with the worker flames before contacting the effluent with the analytical flame; and
(3) detecting emissions from the analytical flame through the detector port using a light detector.

42. The method of claim 41, where each tube has an inner diameter from about 0.05 mm to about 5 mm.

43. The method of claim 42, where the inner diameter is about 0.25 mm.

44. The method of claim 41, where the size of one or more of the flames is from 3 nL to 1 mL.

45. The method of claim 44, where the size of one or more of the flames is about 30 nL.

46. The method of claim 41, where the conduit comprises quartz.

47. The method of claim 41, where the conduit has an inner diameter from about 0.1 mm to about 10 mm.

48. The method of claim 41, where the inner diameter is about 1 mm.

49. The method of claim 41, where the conduit has a length from about 5 mm to about 1,000 mm.

50. The method of claim 41, where the length is about 130 mm.

51. The method of claim 41, where the tubes coupled to the first and second oxygen inlets are positioned along the length of the conduit.

52. The method of claim 41, where the analytical flame is separated from the second worker flame by a first distance of about 2 to about 50 mm.

53. The method of claim 52, where the first distance is about 20 mm.

54. The method of claim 41, where the first worker flame is separated from the second worker flame by a second distance of about 1 mm to about 20 mm.

55. The method of claim 54, where the second distance is about 5 mm.

56. The method of claim 41, where the conduit comprises:
i) a first oxygen inlet,
ii) a second oxygen inlet,
iii) a third oxygen inlet, and
iv) a final oxygen inlet.

57. The method of claim 41, where the conduit comprises:
i) a first oxygen inlet,
ii) a second oxygen inlet,
iii) a third oxygen inlet,
iv) a fourth oxygen inlet, and
v) a final oxygen inlet.

58. The method of claim 41, where the conduit comprises:
i) a first oxygen inlet,
ii) a second oxygen inlet,
iii) a third oxygen inlet,
iv) a fourth oxygen inlet,
v) a fifth oxygen inlet, and
vi) a final oxygen inlet.

59. The method of claim 41, where the hydrogen inlet is positioned closer to the proximal end of the conduit than the oxygen inlets.

60. The method of claim 41, where the method is capable of detecting sulfur at a concentration of less than $1 \times 10^{-10}$ g S/s during use.

61. The method of claim 41, where the method is capable of detecting phosphorus at a concentration of less than $1 \times 10^{-11}$ g P/s during use.

62. The method of claim 41, where the method is capable of maintaining greater than 50% of its original analyte chemiluminescence even in the presence of up to 100 mL/min of hydrocarbon gas flow into the detector during use.

* * * * *

UNITED STATES PATENT AND TRADEMARK OFFICE
CERTIFICATE OF CORRECTION

PATENT NO. : 8,913,239 B2  
APPLICATION NO. : 13/041191  
DATED : December 16, 2014  
INVENTOR(S) : Kevin Thurbide Page 1 of 1

It is certified that error appears in the above-identified patent and that said Letters Patent is hereby corrected as shown below:

In The Claims

In claim 16, column 25, line 25, delete "The mFPD of claim 10" and replace with --The mFPD of claim 15-- therefor.

In claim 18, column 25, line 29, delete "The mFPD of claim 12" and replace with --The mFPD of claim 17-- therefor.

In claim 19, column 25, line 31, delete "The mFPD of claim 13" and replace with --The mFPD of claim 18-- therefor.

In claim 20, column 25, line 33, delete "The mFPD of claim 12" and replace with --The mFPD of claim 17-- therefor.

In claim 21, column 25, line 36, delete "The mFPD of claim 15" and replace with --The mFPD of claim 20-- therefor.

In claim 22, column 25, line 39, delete "The mFPD of claim 16" and replace with --The mFPD of claim 21-- therefor.

Signed and Sealed this  
Seventeenth Day of March, 2015

Michelle K. Lee  
*Director of the United States Patent and Trademark Office*